United States Patent
Hong et al.

(10) Patent No.: US 11,407,982 B2
(45) Date of Patent: Aug. 9, 2022

(54) TRANSAMINASE MUTANT AND USE THEREOF

(71) Applicant: Asymchem Life Science (Tianjin) Co., Ltd, Tianjin (CN)

(72) Inventors: Hao Hong, Tianjin (CN); Gage James, Tianjin (CN); Jiangping Lu, Tianjin (CN); Xuecheng Jiao, Tianjin (CN); Na Zhang, Tianjin (CN); Rui Li, Tianjin (CN); Kejian Zhang, Tianjin (CN)

(73) Assignee: ASYMCHEM LIFE SCIENCE (TIANJIN) CO., LTD, Tianjin (CN)

( * ) Notice: Subject to any disclaimer, the term of this patent is extended or adjusted under 35 U.S.C. 154(b) by 0 days.

(21) Appl. No.: 16/756,649

(22) PCT Filed: Nov. 6, 2017

(86) PCT No.: PCT/CN2017/109500
§ 371 (c)(1),
(2) Date: Apr. 16, 2020

(87) PCT Pub. No.: WO2019/084950
PCT Pub. Date: May 9, 2019

(65) Prior Publication Data
US 2021/0024904 A1 Jan. 28, 2021

(51) Int. Cl.
*C12N 9/06* (2006.01)
*C12N 9/10* (2006.01)
*C12P 13/00* (2006.01)
*C12P 17/12* (2006.01)

(52) U.S. Cl.
CPC .......... *C12N 9/1096* (2013.01); *C12P 13/001* (2013.01); *C12P 17/12* (2013.01); *C12Y 203/01001* (2013.01)

(58) Field of Classification Search
CPC ...... C12N 9/1096; C12P 17/12; C12P 13/001; C12P 17/10; C12P 7/04; C12Y 203/01001; C12Y 206/01036; C12Y 206/01043
USPC ...................................... 435/193, 128, 252.3
See application file for complete search history.

(56) References Cited

U.S. PATENT DOCUMENTS

2016/0298092 A1  10/2016  Shin et al.

FOREIGN PATENT DOCUMENTS

| CN | 104328093 A | 2/2015 |
| CN | 105018440 A | 11/2015 |
| CN | 105441403 A | 3/2016 |
| WO | 0236742 A2 | 5/2002 |
| WO | 0236742 A3 | 8/2003 |
| WO | 2012024104 A2 | 2/2012 |
| WO | 2012024104 A3 | 2/2012 |
| WO | 2016166120 A1 | 10/2016 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340, in IDS.*
Witkowski et al., (Biochemistry 38:11643-11650, 1999.*
Kisselev L., (Structure, 2002, vol. 10: 8-9.*
International Search Report issued for PCT/CN2017/109500, dated Aug. 9, 2018.
GenBank accession No. WP_030166319, version WP_030166319.1, Multispecies: aminotransferase IV [Actinobacteria], Search on Jul. 24, 2018, Search in NCBI [online]: <URL:http://ncbi.nlm.nih.gov/>. Aug. 19, 2015, amino acid sequence; document retrieved Apr. 15, 2020, https://ncbi.nlm.nih.gov/protein/WP_030166319.1/.
Guo, F. et al.; "Transaminase Biocatalysis: Optimization and Application"; Green Chemistry, 2017, vol. 19, pp. 333-360.
Schaetzle et al.; "Enzymatic Asymmetric Synthesis of Enantiomerically Pure Aliphatic, Aromatic and Arylaliphatic Amines with (R)-Selective Amine Transaminases"; Advanced Synthesis & Catalysis, vol. 353, No. 13, Aug. 25, 2011, pp. 2439-2445.
Tortoli, E.; "Aminotransferase IV"; Oct. 25, 2017, XP055707564, Retrieved from the Internet: URL: https://www.uniprot.org/uniprot/A0A1X0ITL2.txt?version=4;[retrieved on Jun. 22, 2020].
Ploux, O.; "Branched-chain amino acid aminotransferase"; Oct. 25, 2017. XP05570567, Retrieved from the Internet URL: https://www.uniprot.org/uniprot/A0A1Y5P4G5.txt?version=3; [retrieved on Jun. 22, 2020].
Anonymous: "UPI000524BF8B"; Aug. 27, 2015, XP055707909, Retrieved from the Internet: URL: https://www.uniprot.org/uniparc/UPI000524BF8B; [retrieved on Jun. 23, 2020].

(Continued)

*Primary Examiner* — Robert B Mondesi
*Assistant Examiner* — Mohammad Y Meah
(74) *Attorney, Agent, or Firm* — ArentFox Schiff LLP

(57) ABSTRACT

Disclosed are transaminase mutants and use thereof. The amino acid sequence of the transaminase mutant is obtained by the mutation of the amino acid sequence as shown in SEQ ID NO: 1, and the mutation at least comprises one of the following mutation sites: the 19-th site, the 41-th site, the 43-th site, the 72-th site, the 76-th site, the 92-th site, the 107-th site, the 125-th site, the 132-th site, the 226-th site, the 292-th site, the 295-th site, the 308-th site, and the 332-th site; and the 19-th site is mutated into a serine, the 41-th site is mutated into a serine, the 43-th site is mutated into an asparagine, a glycine in the 72-th site is mutated into a leucine, etc.; or the amino acid sequence of the transaminase mutant has the mutation sites in the mutated amino acid sequence, and has more than 80% homology to the mutated amino acid sequence.

6 Claims, No Drawings
Specification includes a Sequence Listing.

(56) References Cited

OTHER PUBLICATIONS

Supplementary European Search Report issued in EP Application No. 17 93 0421, date of completion of search Jun. 23, 2020.

* cited by examiner

SEQUENCE LISTING

```
<160> NUMBER OF SEQ ID NOS: 60

<210> SEQ ID NO 1
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 1

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
                20                  25                  30

Gln Tyr Ser Asp Tyr Glu Leu Asp Glu Ser Ser Pro Phe Ala Gly Gly
            35                  40                  45

Ala Ala Trp Ile Glu Gly Glu Tyr Val Pro Ala Ala Glu Ala Arg Ile
        50                  55                  60

Ser Leu Phe Asp Thr Gly Phe Gly His Ser Asp Leu Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ser Leu Ser Gln
        115                 120                 125

Leu Arg Glu Ser Phe Val Asn Ile Thr Ile Thr Arg Gly Tyr Gly Ala
    130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
```

```
            165                 170                 175
Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
    210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
            245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
            275                 280                 285

Leu Ile Ala Val Thr Thr Ala Gly Gly Ile Thr Pro Ile Thr Ser Leu
        290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
            325                 330                 335

Glu Ala Ile Glu Tyr
            340

<210> SEQ ID NO 2
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 2

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Ser Pro Phe Ala Gly Gly
        35                  40                  45

Ala Ala Trp Ile Glu Gly Glu Tyr Val Pro Ala Ala Glu Ala Arg Ile
    50                  55                  60

Ser Leu Phe Asp Thr Gly Phe Gly His Ser Asp Ala Thr Tyr Thr Val
65                  70                  75                  80

Ala His Val Trp His Gly Asn Ile Phe Arg Leu Lys Asp His Ile Asp
            85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ser Leu Ser Gln
            115                 120                 125

Leu Ala Glu Ser Phe Val Asn Ile Thr Ile Thr Arg Gly Tyr Gly Ala
        130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
            165                 170                 175

Gly Thr Ser Ala Ile Val Pro Arg His Val Arg Arg Ala Gly Arg Asn
```

```
            180                 185                 190
Thr Val Asp Pro Thr Val Lys Asn Tyr Gln Trp Gly Asp Leu Thr Ala
            195                 200                 205
Ala Ser Phe Glu Ala Lys Asp Arg Gly Ala Arg Thr Ala Ile Leu Leu
        210                 215                 220
Asp Ala Asp Asn Cys Val Ala Glu Gly Pro Gly Phe Asn Val Val Met
225                 230                 235                 240
Val Lys Asp Gly Lys Leu Ser Ser Pro Ser Arg Asn Ala Leu Pro Gly
                245                 250                 255
Ile Thr Arg Leu Thr Val Met Glu Met Ala Asp Glu Met Gly Ile Glu
            260                 265                 270
Phe Thr Leu Arg Asp Ile Thr Ser Arg Glu Leu Tyr Glu Ala Asp Glu
        275                 280                 285
Leu Ile Ala Cys Thr Thr Gly Gly Ile Thr Pro Ile Thr Ser Leu
        290                 295                 300
Asp Gly Glu Pro Leu Gly Asp Gly Thr Pro Gly Pro Val Thr Val Ala
305                 310                 315                 320
Ile Arg Asp Arg Phe Trp Ala Met Met Asp Glu Pro Ser Ser Leu Val
                325                 330                 335
Glu Ala Ile Glu Tyr
            340

<210> SEQ ID NO 3
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 3

Met Thr Ile Ser Lys Asp Ile Asp Tyr Ser Thr Ser Asn Leu Val Ser
1               5                   10                  15
Val Ala Pro Gly Ala Ile Arg Glu Pro Thr Pro Ala Gly Ser Val Ile
            20                  25                  30
Gln Tyr Ser Asp Tyr Glu Leu Asp Glu Ser Ser Pro Phe Ala Gly Gly
        35                  40                  45
Ala Ala Trp Ile Glu Gly Glu Tyr Val Pro Ala Ala Glu Ala Arg Ile
    50                  55                  60
Ser Leu Phe Asp Thr Gly Phe Gly His Ser Asp Leu Thr Tyr Thr Val
65                  70                  75                  80
Ala His Val Trp His Gly Asn Ile Phe Arg Leu Lys Asp His Ile Asp
                85                  90                  95
Arg Val Phe Asp Gly Ala Gln Lys Leu Arg Ile Gln Ser Pro Leu Thr
            100                 105                 110
Lys Ala Glu Val Glu Asp Ile Thr Lys Arg Cys Val Ser Leu Ser Gln
        115                 120                 125
Leu Arg Glu Ser Phe Val Asn Ile Thr Ile Thr Arg Gly Tyr Gly Ala
    130                 135                 140
Arg Lys Gly Glu Lys Asp Leu Ser Lys Leu Thr Ser Gln Ile Tyr Ile
145                 150                 155                 160
Tyr Ala Ile Pro Tyr Leu Trp Ala Phe Pro Pro Glu Glu Gln Ile Phe
                165                 170                 175
Gly Thr Ser Ala Ile Val Pro Arg His Val Arg Arg Ala Gly Arg Asn
            180                 185                 190
Thr Val Asp Pro Thr Val Lys Asn Tyr Gln Trp Gly Asp Leu Thr Ala
```

```
                195                 200                 205
Ala Ser Phe Glu Ala Lys Asp Arg Gly Ala Arg Thr Ala Ile Leu Leu
210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
                260                 265                 270

Phe Thr Leu Arg Asp Ile Thr Ser Arg Glu Leu Tyr Glu Ala Asp Glu
                275                 280                 285

Leu Ile Ala Val Thr Thr Gly Gly Ile Thr Pro Ile Thr Ser Leu
290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
                340

<210> SEQ ID NO 4
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 4

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
                20                  25                  30

Gln Tyr Ser Asp Tyr Glu Leu Asp Glu Ser Asn Pro Phe Ala Gly Gly
                35                  40                  45

Ala Ala Trp Ile Glu Gly Glu Tyr Val Pro Ala Ala Glu Ala Arg Ile
            50                  55                  60

Ser Leu Phe Asp Thr Gly Phe Leu His Ser Asp Leu Thr Tyr Thr Val
65              70                  75                  80

Ala His Val Trp His Gly Asn Ile Phe Arg Leu Lys Asp His Ile Asp
                    85                  90                  95

Arg Val Phe Asp Gly Ala Gln Lys Leu Arg Leu Gln Ser Pro Leu Thr
                100                 105                 110

Lys Ala Glu Val Glu Asp Ile Thr Lys Arg Cys Val Ser Leu Ser Gln
                115                 120                 125

Leu Arg Glu Ser Phe Val Asn Ile Thr Ile Thr Arg Gly Tyr Gly Ala
            130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
                180                 185                 190

Thr Val Asp Pro Thr Val Lys Asn Tyr Gln Trp Gly Asp Leu Thr Ala
                195                 200                 205

Ala Ser Phe Glu Ala Lys Asp Arg Gly Ala Arg Thr Ala Ile Leu Leu
```

```
            210                 215                 220
Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
                260                 265                 270

Phe Thr Leu Arg Asp Ile Thr Ser Arg Glu Leu Tyr Glu Ala Asp Glu
                275                 280                 285

Leu Ile Ala Val Thr Thr Gly Gly Ile Thr Pro Ile Thr Ser Leu
290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
                340

<210> SEQ ID NO 5
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 5

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
                20                  25                  30

Gln Tyr Ser Asp Tyr Glu Leu Asp Glu Ser Ser Pro Phe Ala Gly Gly
                35                  40                  45

Ala Ala Trp Ile Glu Gly Glu Tyr Val Pro Ala Ala Glu Ala Arg Ile
            50                  55                  60

Ser Leu Phe Asp Thr Gly Phe Gly His Ser Asp Leu Thr Tyr Thr Val
65                  70                  75                  80

Ala His Val Trp His Gly Asn Ile Phe Arg Leu Lys Asp His Ile Asn
                85                  90                  95

Arg Val Phe Asp Gly Ala Gln Ile Leu Arg Leu Gln Ser Pro Leu Thr
                100                 105                 110

Lys Ala Glu Val Glu Asp Ile Thr Lys Arg Cys Val Ser Leu Ser Gln
            115                 120                 125

Leu Arg Glu Ser Phe Val Asn Ile Thr Ile Thr Arg Gly Tyr Gly Ala
130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
                180                 185                 190

Thr Val Asp Pro Thr Val Lys Asn Tyr Gln Trp Gly Asp Leu Thr Ala
            195                 200                 205

Ala Ser Phe Glu Ala Lys Asp Arg Gly Ala Arg Thr Ala Ile Leu Leu
210                 215                 220

Asp Ala Asp Asn Cys Val Ala Glu Gly Pro Gly Phe Asn Val Val Met
```

-continued

```
                225                 230                 235                 240
Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
                260                 265                 270

Phe Thr Leu Arg Asp Ile Thr Ser Arg Glu Leu Tyr Glu Ala Asp Glu
                275                 280                 285

Leu Ile Ala Val Thr Thr Gly Gly Ile Thr Pro Ile Thr Ser Leu
                290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
                340

<210> SEQ ID NO 6
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 6

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
                20                  25                  30

Gln Tyr Ser Asp Tyr Glu Leu Asp Glu Ser Ser Pro Phe Ala Gly Gly
                35                  40                  45

Ala Ala Trp Ile Glu Gly Glu Tyr Val Pro Ala Ala Glu Ala Arg Ile
                50                  55                  60

Ser Leu Phe Asp Thr Gly Phe Gly His Ser Asp Ala Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
                100                 105                 110

Lys Ala Glu Val Glu Asp Ile Thr Lys Arg Cys Val Ala Leu Ser Gln
                115                 120                 125

Leu Arg Glu Ser Phe Val Asn Ile Thr Ile Thr Arg Gly Tyr Gly Ala
                130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Ala Gly Arg Asn
                180                 185                 190

Thr Val Asp Pro Thr Val Lys Asn Tyr Gln Trp Gly Asp Leu Thr Ala
                195                 200                 205

Ala Ser Phe Glu Ala Lys Asp Arg Gly Ala Arg Thr Ala Ile Leu Leu
                210                 215                 220

Asp Gly Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
```

```
                    245                 250                 255
Ile Thr Arg Leu Thr Val Met Glu Met Ala Asp Glu Met Gly Ile Glu
                260                 265                 270

Phe Thr Leu Arg Asp Ile Thr Ser Arg Glu Leu Tyr Glu Ala Asp Glu
            275                 280                 285

Leu Ile Ala Val Thr Thr Gly Gly Ile Thr Pro Ile Thr Ser Leu
        290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
                340

<210> SEQ ID NO 7
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 7

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Ser Pro Phe Ala Gly Gly
        35                  40                  45

Ala Ala Trp Ile Glu Gly Glu Tyr Val Pro Ala Ala Glu Ala Arg Ile
    50                  55                  60

Ser Leu Phe Asp Thr Gly Phe Gly His Ser Asp Ala Thr Tyr Thr Val
65              70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ala Leu Ser Gln
        115                 120                 125

Leu Arg Glu Ala Phe Val Asn Ile Thr Ile Thr Arg Gly Tyr Gly Ala
    130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
    210                 215                 220

Asp Gly Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
```

```
            260                 265                 270
Phe Thr Leu Arg Asp Ile Thr Ser Arg Glu Leu Tyr Glu Ala Asp Glu
            275                 280                 285

Leu Ile Ala Val Thr Thr Gly Gly Ile Thr Pro Ile Thr Ser Leu
            290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                    325                 330                 335

Glu Ala Ile Glu Tyr
                340

<210> SEQ ID NO 8
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 8

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
                20                  25                  30

Gln Tyr Ser Asp Tyr Glu Leu Asp Glu Ser Ser Pro Phe Ala Gly Gly
            35                  40                  45

Ala Ala Trp Ile Glu Gly Glu Tyr Val Pro Ala Ala Glu Ala Arg Ile
        50                  55                  60

Ser Leu Phe Asp Thr Gly Phe Gly His Ser Asp Leu Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
                100                 105                 110

Lys Ala Glu Val Glu Asp Ile Thr Lys Arg Cys Val Ser Leu Ser Gln
            115                 120                 125

Leu Arg Glu Ala Phe Val Asn Ile Thr Ile Thr Arg Gly Tyr Gly Ala
130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
    210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
```

```
                275                 280                 285
Leu Ile Ala Val Thr Thr Gly Gly Ile Thr Pro Ile Thr Ser Leu
        290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
            340

<210> SEQ ID NO 9
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 9

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Ser Pro Phe Ala Gly Gly
        35                  40                  45

Ala Ala Trp Ile Glu Gly Glu Tyr Val Pro Ala Ala Glu Ala Arg Ile
    50                  55                  60

Ser Leu Phe Asp Thr Gly Phe Leu His Ser Asp Leu Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ser Leu Ser Gln
        115                 120                 125

Leu Arg Glu Ser Phe Val Asn Ile Thr Ile Thr Arg Gly Tyr Gly Ala
    130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
    210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Val Thr Thr Gly Gly Ile Thr Pro Ile Thr Ser Leu
```

```
                290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
            340

<210> SEQ ID NO 10
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 10

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
                20                  25                  30

Gln Tyr Ser Asp Tyr Glu Leu Asp Glu Ser Ser Pro Phe Ala Gly Gly
            35                  40                  45

Ala Ala Trp Ile Glu Gly Glu Tyr Val Pro Ala Ala Glu Ala Arg Ile
        50                  55                  60

Ser Leu Phe Asp Thr Gly Phe Leu His Ser Asp Leu Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
                100                 105                 110

Lys Ala Glu Val Glu Asp Ile Thr Lys Arg Cys Val Ser Leu Ser Gln
            115                 120                 125

Leu Arg Glu Ala Phe Val Asn Ile Thr Ile Thr Arg Gly Tyr Gly Ala
        130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Val Thr Thr Gly Gly Ile Thr Pro Ile Thr Ser Leu
        290                 295                 300

Asp Gly Glu Pro Leu Gly Asp Gly Thr Pro Gly Pro Val Thr Val Ala
```

```
305                 310                 315                 320
Ile Arg Asp Arg Phe Trp Ala Met Met Asp Glu Pro Ser Ser Leu Val
                325                 330                 335

Glu Ala Ile Glu Tyr
            340

<210> SEQ ID NO 11
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 11

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
                20                  25                  30

Gln Tyr Ser Asp Tyr Glu Leu Asp Glu Ser Ser Pro Phe Ala Gly Gly
            35                  40                  45

Ala Ala Trp Ile Glu Gly Glu Tyr Val Pro Ala Ala Glu Ala Arg Ile
        50                  55                  60

Ser Leu Phe Asp Thr Gly Phe Leu His Ser Asp Leu Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ser Leu Ser Gln
        115                 120                 125

Leu Arg Glu Ser Phe Val Asn Ile Thr Ile Thr Arg Gly Tyr Gly Ala
130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Cys Thr Thr Gly Gly Gly Ile Thr Pro Ile Thr Ser Leu
290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
```

```
                            325                 330                 335

Glu Ala Ile Glu Tyr
            340

<210> SEQ ID NO 12
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 12

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Ser Pro Phe Ala Gly Gly
        35                  40                  45

Ala Ala Trp Ile Glu Gly Glu Tyr Val Pro Ala Ala Glu Ala Arg Ile
    50                  55                  60

Ser Leu Phe Asp Thr Gly Phe Leu His Ser Asp Ala Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ser Leu Ser Gln
        115                 120                 125

Leu Arg Glu Ser Phe Val Asn Ile Thr Ile Thr Arg Gly Tyr Gly Ala
    130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
    210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Cys Thr Thr Gly Gly Ile Thr Pro Ile Thr Ser Leu
    290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
            340
```

<210> SEQ ID NO 13
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 13

```
Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Ser Pro Phe Ala Gly Gly
        35                  40                  45

Ala Ala Trp Ile Glu Gly Glu Tyr Val Pro Ala Ala Glu Ala Arg Ile
    50                  55                  60

Ser Leu Phe Asp Thr Gly Phe Leu His Ser Asp Leu Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ser Leu Ser Gln
        115                 120                 125

Leu Arg Glu Ser Phe Val Asn Ile Thr Ile Thr Arg Gly Tyr Gly Ala
    130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
    210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Val Thr Thr Ala Gly Gly Ile Thr Pro Ile Thr Ser Leu
    290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Pro Ser Ser Leu Val
                325                 330                 335

Glu Ala Ile Glu Tyr
            340
```

```
<210> SEQ ID NO 14
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 14
```

| | | | | | | | | | | | | | | |
|---|---|---|---|---|---|---|---|---|---|---|---|---|---|---|
|Met|Thr|Ile|Ser|Lys|Asp|Ile|Asp|Tyr|Ser|Thr|Ser|Asn|Leu|Val|Ser|
|1| | | |5| | | | |10| | | | |15| |

| | | | | | | | | | | | | | | | |
|---|---|---|---|---|---|---|---|---|---|---|---|---|---|---|---|
|Val|Ala|Pro|Gly|Ala|Ile|Arg|Glu|Pro|Thr|Pro|Ala|Gly|Ser|Val|Ile|
| | | | |20| | | | |25| | | | |30| |

| | | | | | | | | | | | | | | | |
|---|---|---|---|---|---|---|---|---|---|---|---|---|---|---|---|
|Gln|Tyr|Ser|Asp|Tyr|Glu|Leu|Asp|Glu|Ser|Ser|Pro|Phe|Ala|Gly|Gly|
| | | | |35| | | | |40| | | | |45| |

| | | | | | | | | | | | | | | | |
|---|---|---|---|---|---|---|---|---|---|---|---|---|---|---|---|
|Ala|Ala|Trp|Ile|Glu|Gly|Glu|Tyr|Val|Pro|Ala|Ala|Glu|Ala|Arg|Ile|
| | | | |50| | | | |55| | | | |60| |

| | | | | | | | | | | | | | | | |
|---|---|---|---|---|---|---|---|---|---|---|---|---|---|---|---|
|Ser|Leu|Phe|Asp|Thr|Gly|Phe|Gly|His|Ser|Asp|Ala|Thr|Tyr|Thr|Val|
|65| | | | |70| | | | |75| | | | |80|

| | | | | | | | | | | | | | | | |
|---|---|---|---|---|---|---|---|---|---|---|---|---|---|---|---|
|Ala|His|Val|Trp|His|Gly|Asn|Ile|Phe|Arg|Leu|Lys|Asp|His|Ile|Asp|
| | | | |85| | | | |90| | | | |95| |

| | | | | | | | | | | | | | | | |
|---|---|---|---|---|---|---|---|---|---|---|---|---|---|---|---|
|Arg|Val|Phe|Asp|Gly|Ala|Gln|Lys|Leu|Arg|Leu|Gln|Ser|Pro|Leu|Thr|
| | | |100| | | | |105| | | | |110| | |

| | | | | | | | | | | | | | | | |
|---|---|---|---|---|---|---|---|---|---|---|---|---|---|---|---|
|Lys|Ala|Glu|Val|Glu|Asp|Ile|Thr|Lys|Arg|Cys|Val|Ser|Leu|Ser|Gln|
| | | |115| | | | |120| | | | |125| | |

| | | | | | | | | | | | | | | | |
|---|---|---|---|---|---|---|---|---|---|---|---|---|---|---|---|
|Leu|Arg|Glu|Ser|Phe|Val|Asn|Ile|Thr|Ile|Thr|Arg|Gly|Tyr|Gly|Ala|
| | | |130| | | | |135| | | | |140| | |

| | | | | | | | | | | | | | | | |
|---|---|---|---|---|---|---|---|---|---|---|---|---|---|---|---|
|Arg|Lys|Gly|Glu|Lys|Asp|Leu|Ser|Lys|Leu|Thr|Ser|Gln|Ile|Tyr|Ile|
|145| | | | |150| | | | |155| | | | |160|

| | | | | | | | | | | | | | | | |
|---|---|---|---|---|---|---|---|---|---|---|---|---|---|---|---|
|Tyr|Ala|Ile|Pro|Tyr|Leu|Trp|Ala|Phe|Pro|Pro|Glu|Glu|Gln|Ile|Phe|
| | | | |165| | | | |170| | | | |175| |

| | | | | | | | | | | | | | | | |
|---|---|---|---|---|---|---|---|---|---|---|---|---|---|---|---|
|Gly|Thr|Ser|Ala|Ile|Val|Pro|Arg|His|Val|Arg|Arg|Ala|Gly|Arg|Asn|
| | | |180| | | | |185| | | | |190| | |

| | | | | | | | | | | | | | | | |
|---|---|---|---|---|---|---|---|---|---|---|---|---|---|---|---|
|Thr|Val|Asp|Pro|Thr|Val|Lys|Asn|Tyr|Gln|Trp|Gly|Asp|Leu|Thr|Ala|
| | | |195| | | | |200| | | | |205| | |

| | | | | | | | | | | | | | | | |
|---|---|---|---|---|---|---|---|---|---|---|---|---|---|---|---|
|Ala|Ser|Phe|Glu|Ala|Lys|Asp|Arg|Gly|Ala|Arg|Thr|Ala|Ile|Leu|Leu|
| | | |210| | | | |215| | | | |220| | |

| | | | | | | | | | | | | | | | |
|---|---|---|---|---|---|---|---|---|---|---|---|---|---|---|---|
|Asp|Ala|Asp|Asn|Cys|Val|Ala|Glu|Gly|Pro|Gly|Phe|Asn|Val|Val|Met|
|225| | | | |230| | | | |235| | | | |240|

| | | | | | | | | | | | | | | | |
|---|---|---|---|---|---|---|---|---|---|---|---|---|---|---|---|
|Val|Lys|Asp|Gly|Lys|Leu|Ser|Ser|Pro|Ser|Arg|Asn|Ala|Leu|Pro|Gly|
| | | |245| | | | |250| | | | |255| | |

| | | | | | | | | | | | | | | | |
|---|---|---|---|---|---|---|---|---|---|---|---|---|---|---|---|
|Ile|Thr|Arg|Leu|Thr|Val|Met|Glu|Met|Ala|Asp|Glu|Met|Gly|Ile|Glu|
| | | |260| | | | |265| | | | |270| | |

| | | | | | | | | | | | | | | | |
|---|---|---|---|---|---|---|---|---|---|---|---|---|---|---|---|
|Phe|Thr|Leu|Arg|Asp|Ile|Thr|Ser|Arg|Glu|Leu|Tyr|Glu|Ala|Asp|Glu|
| | | |275| | | | |280| | | | |285| | |

| | | | | | | | | | | | | | | | |
|---|---|---|---|---|---|---|---|---|---|---|---|---|---|---|---|
|Leu|Ile|Ala|Val|Thr|Thr|Ala|Gly|Gly|Ile|Thr|Pro|Ile|Thr|Ser|Leu|
| | | |290| | | | |295| | | | |300| | |

| | | | | | | | | | | | | | | | |
|---|---|---|---|---|---|---|---|---|---|---|---|---|---|---|---|
|Asp|Gly|Glu|Pro|Leu|Gly|Asp|Gly|Thr|Pro|Gly|Pro|Val|Thr|Val|Ala|
|305| | | | |310| | | | |315| | | | |320|

| | | | | | | | | | | | | | | | |
|---|---|---|---|---|---|---|---|---|---|---|---|---|---|---|---|
|Ile|Arg|Asp|Arg|Phe|Trp|Ala|Met|Met|Asp|Glu|Pro|Ser|Ser|Leu|Val|
| | | |325| | | | |330| | | | |335| | |

| | | | |
|---|---|---|---|
|Glu|Ala|Ile|Glu|Tyr|
| | | |340| |

```
<210> SEQ ID NO 15
<211> LENGTH: 341
<212> TYPE: PRT
```

<213> ORGANISM: Unknown
<220> FEATURE:
<223> OTHER INFORMATION: Bacteria of the phylum Actinobacteria.

<400> SEQUENCE: 15

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Ser Pro Phe Ala Gly Gly
        35                  40                  45

Ala Ala Trp Ile Glu Gly Glu Tyr Val Pro Ala Ala Glu Ala Arg Ile
50                  55                  60

Ser Leu Phe Asp Thr Gly Phe Gly His Ser Asp Leu Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Ile Gln Ser Pro Leu Thr
            100                 105                 110

Lys Ala Glu Val Glu Asp Ile Thr Lys Arg Cys Val Ser Leu Ser Gln
        115                 120                 125

Leu Arg Glu Ser Phe Val Asn Ile Thr Ile Thr Arg Gly Tyr Gly Ala
130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Val Thr Thr Ala Gly Gly Ile Thr Pro Ile Thr Ser Leu
290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Pro Ser Ser Leu Val
                325                 330                 335

Glu Ala Ile Glu Tyr
            340

<210> SEQ ID NO 16
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 16

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
                20                  25                  30

Gln Tyr Ser Asp Tyr Glu Leu Asp Glu Ser Ser Pro Phe Ala Gly Gly
            35                  40                  45

Ala Ala Trp Ile Glu Gly Glu Tyr Val Pro Ala Ala Glu Ala Arg Ile
        50                  55                  60

Ser Leu Phe Asp Thr Gly Phe Gly His Ser Asp Leu Thr Tyr Thr Val
65                  70                  75                  80

Ala His Val Trp His Gly Asn Ile Phe Arg Leu Gly Asp His Ile Asp
                    85                  90                  95

Arg Val Phe Asp Gly Ala Gln Lys Leu Arg Leu Gln Ser Pro Leu Thr
                100                 105                 110

Lys Ala Glu Val Glu Asp Ile Thr Lys Arg Cys Val Ser Leu Ser Gln
            115                 120                 125

Leu Arg Glu Ser Phe Val Asn Ile Thr Ile Thr Arg Gly Tyr Gly Ala
            130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
                195                 200                 205

Ala Ser Phe Glu Ala Lys Asp Arg Gly Ala Arg Thr Ala Ile Leu Leu
        210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
            275                 280                 285

Leu Ile Ala Val Thr Thr Ala Gly Gly Ile Thr Pro Ile Thr Ser Leu
        290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
            340

<210> SEQ ID NO 17
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 17

```
Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Ser Pro Phe Ala Gly Gly
            35                  40                  45

Ala Ala Trp Ile Glu Gly Glu Tyr Val Pro Ala Ala Glu Ala Arg Ile
        50                  55                  60

Ser Leu Phe Asp Thr Gly Phe Gly His Ser Asp Leu Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
                100                 105                 110

Lys Ala Glu Val Glu Asp Ile Thr Lys Arg Cys Val Ala Leu Ser Gln
            115                 120                 125

Leu Arg Glu Ser Phe Val Asn Ile Thr Ile Thr Arg Gly Tyr Gly Ala
        130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
            195                 200                 205

Ala Ser Phe Glu Ala Lys Asp Arg Gly Ala Arg Thr Ala Ile Leu Leu
        210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
            245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Val Thr Thr Ala Gly Gly Ile Thr Pro Ile Thr Ser Leu
        290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
            340

<210> SEQ ID NO 18
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 18

Met Thr Ile Ser Lys Asp Ile Asp Tyr Ser Thr Ser Asn Leu Val Ser
1               5                   10                  15
```

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Ser Pro Phe Ala Gly Gly
        35                  40                  45

Ala Ala Trp Ile Glu Gly Glu Tyr Val Pro Ala Ala Glu Ala Arg Ile
50                  55                  60

Ser Leu Phe Asp Thr Gly Phe Gly His Ser Asp Leu Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ser Leu Ser Gln
        115                 120                 125

Leu Arg Glu Ala Phe Val Asn Ile Thr Ile Thr Arg Gly Tyr Gly Ala
    130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
    210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Val Thr Thr Ala Gly Gly Ile Thr Pro Ile Thr Ser Leu
    290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
            340

<210> SEQ ID NO 19
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 19

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

```
Gln Tyr Ser Asp Tyr Glu Leu Asp Glu Ser Ser Pro Phe Ala Gly Gly
         35                  40                  45

Ala Ala Trp Ile Glu Gly Glu Tyr Val Pro Ala Glu Ala Arg Ile
 50                  55                  60

Ser Leu Phe Asp Thr Gly Phe Gly His Ser Asp Leu Thr Tyr Thr Val
 65                  70                  75                  80

Ala His Val Trp His Gly Asn Ile Phe Arg Leu Lys Asp His Ile Asp
                 85                  90                  95

Arg Val Phe Asp Gly Ala Gln Lys Leu Arg Leu Gln Ser Pro Leu Thr
                100                 105                 110

Lys Ala Glu Val Glu Asp Ile Thr Lys Arg Cys Val Ser Leu Ser Gln
            115                 120                 125

Leu Arg Glu Ser Phe Val Asn Ile Thr Ile Thr Arg Gly Tyr Gly Ala
        130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
    210                 215                 220

Asp Gly Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Val Thr Thr Ala Gly Gly Ile Thr Pro Ile Thr Ser Leu
    290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
            340

<210> SEQ ID NO 20
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 20

Met Thr Ile Ser Lys Asp Ile Asp Tyr Ser Thr Ser Asn Leu Val Ser
1               5                  10                  15

Val Ala Pro Gly Ala Ile Arg Glu Pro Thr Pro Ala Gly Ser Val Ile
                20                  25                  30

Gln Tyr Ser Asp Tyr Glu Leu Asp Glu Ser Ser Pro Phe Ala Gly Gly
            35                  40                  45
```

Ala Ala Trp Ile Glu Gly Glu Tyr Val Pro Ala Ala Glu Ala Arg Ile
50                  55                  60

Ser Leu Phe Asp Thr Gly Phe Gly His Ser Asp Leu Thr Tyr Thr Val
65                  70                  75                  80

Ala His Val Trp His Gly Asn Ile Phe Arg Leu Lys Asp His Ile Asp
            85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ser Leu Ser Gln
            115                 120                 125

Leu Arg Glu Ser Phe Val Asn Ile Thr Ile Thr Arg Gly Tyr Gly Ala
130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Gln Ile Phe
                165                 170                 175

Gly Thr Ser Ala Ile Val Pro Arg His Val Arg Ala Gly Arg Asn
            180                 185                 190

Thr Val Asp Pro Thr Val Lys Asn Tyr Gln Trp Gly Asp Leu Thr Ala
            195                 200                 205

Ala Ser Phe Glu Ala Lys Asp Arg Gly Ala Arg Thr Ala Ile Leu Leu
210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
            245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
            275                 280                 285

Leu Ile Ala Cys Thr Thr Ala Gly Gly Ile Thr Pro Ile Thr Ser Leu
290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
            325                 330                 335

Glu Ala Ile Glu Tyr
            340

<210> SEQ ID NO 21
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 21

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Ser Pro Phe Ala Gly Gly
            35                  40                  45

Ala Ala Trp Ile Glu Gly Glu Tyr Val Pro Ala Ala Glu Ala Arg Ile
50                  55                  60

```
Ser Leu Phe Asp Thr Gly Phe Gly His Ser Asp Leu Thr Tyr Thr Val
 65                  70                  75                  80

Ala His Val Trp His Gly Asn Ile Phe Arg Leu Lys Asp His Ile Asp
                 85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ser Leu Ser Gln
        115                 120                 125

Leu Arg Glu Ser Phe Val Asn Ile Thr Ile Thr Arg Gly Tyr Gly Ala
    130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
    210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Val Thr Thr Gly Gly Gly Ile Thr Pro Ile Thr Ser Leu
    290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
            340

<210> SEQ ID NO 22
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 22

Met Thr Ile Ser Lys Asp Ile Asp Tyr Ser Thr Ser Asn Leu Val Ser
  1               5                  10                  15

Val Ala Ser Gly Ala Ile Arg Glu Pro Thr Pro Ala Gly Ser Val Ile
                 20                  25                  30

Gln Tyr Ser Asp Tyr Glu Leu Asp Glu Ser Ser Pro Phe Ala Gly Gly
             35                  40                  45

Ala Ala Trp Ile Glu Gly Glu Tyr Val Pro Ala Ala Glu Ala Arg Ile
         50                  55                  60

Ser Leu Phe Asp Thr Gly Phe Gly His Ser Asp Leu Thr Tyr Thr Val
 65                  70                  75                  80
```

```
Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ser Leu Ser Gln
        115                 120                 125

Leu Arg Glu Ser Phe Val Asn Ile Thr Ile Thr Arg Gly Tyr Gly Ala
    130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
    210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Val Thr Thr Ala Gly Gly Ile Thr Pro Ile Thr Ser Leu
    290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Pro Ser Ser Leu Val
                325                 330                 335

Glu Ala Ile Glu Tyr
            340

<210> SEQ ID NO 23
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 23

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Ser Ser Pro Phe Ala Gly Gly
        35                  40                  45

Ala Ala Trp Ile Glu Gly Glu Tyr Val Pro Ala Ala Glu Ala Arg Ile
    50                  55                  60

Ser Leu Phe Asp Thr Gly Phe Gly His Ser Asp Leu Thr Tyr Thr Val
65                  70                  75                  80

Ala His Val Trp His Gly Asn Ile Phe Arg Leu Lys Asp His Ile Asp
                85                  90                  95
```

```
Arg Val Phe Asp Gly Ala Gln Lys Leu Arg Leu Gln Ser Pro Leu Thr
                100                 105                 110

Lys Ala Glu Val Glu Asp Ile Thr Lys Arg Cys Val Ser Leu Ser Gln
            115                 120                 125

Leu Arg Glu Ser Phe Val Asn Ile Thr Ile Thr Arg Gly Tyr Gly Ala
        130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Val Thr Thr Ala Gly Gly Ile Thr Pro Ile Thr Ser Leu
290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
            340

<210> SEQ ID NO 24
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 24

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Asn Pro Phe Ala Gly Gly
        35                  40                  45

Ala Ala Trp Ile Glu Gly Glu Tyr Val Pro Ala Ala Gly Ala Arg Ile
    50                  55                  60

Ser Leu Phe Asp Thr Gly Phe Gly His Ser Asp Leu Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
                100                 105                 110
```

```
Lys Ala Glu Val Glu Asp Ile Thr Lys Arg Cys Val Ser Leu Ser Gln
            115                 120                 125

Leu Arg Glu Ser Phe Val Asn Ile Thr Ile Thr Arg Gly Tyr Gly Ala
        130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
    210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
        260                 265                 270

Phe Thr Leu Arg Asp Ile Thr Ser Arg Glu Leu Tyr Glu Ala Asp Glu
    275                 280                 285

Leu Ile Ala Val Thr Thr Ala Gly Gly Ile Thr Pro Ile Thr Ser Leu
    290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
            340

<210> SEQ ID NO 25
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 25

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
                20                  25                  30

Gln Tyr Ser Asp Tyr Glu Leu Asp Glu Ser Ser Pro Phe Ala Gly Gly
            35                  40                  45

Ala Ala Trp Ile Glu Gly Glu Tyr Val Pro Ala Ala Glu Ala Arg Ile
        50                  55                  60

Ser Leu Phe Asp Thr Gly Phe Gly His Ser Asp Leu Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ser Leu Ser Gln
        115                 120                 125
```

```
Leu Arg Glu Ser Phe Val Asn Ile Thr Ile Thr Arg Gly Tyr Gly Ala
    130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Val Thr Thr Ala Gly Gly Ile Thr Pro Ile Thr Ser Leu
290                 295                 300

Asp Gly Glu Ser Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
            340

<210> SEQ ID NO 26
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 26

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
                20                  25                  30

Gln Tyr Ser Asp Tyr Glu Leu Asp Ser Ser Pro Phe Ala Gly Gly
            35                  40                  45

Ala Ala Trp Ile Glu Gly Glu Tyr Val Pro Ala Ala Glu Ala Arg Ile
50                  55                  60

Ser Leu Phe Asp Thr Gly Phe Gly His Ser Asp Leu Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ser Leu Ser Gln
        115                 120                 125

Leu Arg Glu Ser Phe Val Asn Ile Thr Ile Thr Arg Gly Tyr Gly Ala
    130                 135                 140
```

```
Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Glu Glu Gln Ile Phe
            165                 170                 175

Gly Thr Ser Ala Ile Val Pro Arg His Val Arg Ala Gly Arg Asn
            180                 185                 190

Thr Val Asp Pro Thr Val Lys Asn Tyr Gln Trp Gly Asp Leu Thr Ala
            195                 200                 205

Ala Ser Phe Glu Ala Lys Asp Arg Gly Ala Arg Thr Ala Ile Leu Leu
            210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
            245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
            275                 280                 285

Leu Ile Ala Val Thr Thr Ala Gly Gly Ile Thr Pro Ile Thr Ser Leu
            290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Ser Ser Leu Val
            325                 330                 335

Glu Ala Ile Glu Tyr
            340

<210> SEQ ID NO 27
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 27

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Ser Pro Phe Ala Gly Gly
            35                  40                  45

Ala Ala Trp Ile Glu Gly Glu Tyr Val Pro Ala Ala Gly Ala Arg Ile
    50                  55                  60

Ser Leu Phe Asp Thr Gly Phe Gly His Ser Asp Ala Thr Tyr Thr Val
65                  70                  75                  80

Ala His Val Trp His Gly Asn Ile Phe Arg Leu Lys Asp His Ile Asp
            85                  90                  95

Arg Val Phe Asp Gly Ala Gln Lys Leu Arg Ile Gln Ser Gln Leu Thr
            100                 105                 110

Lys Ala Glu Val Glu Asp Ile Thr Lys Arg Cys Val Ser Leu Ser Gln
            115                 120                 125

Leu Arg Glu Ser Phe Val Asn Ile Thr Ile Thr Arg Gly Tyr Gly Ala
            130                 135                 140

Arg Lys Gly Glu Lys Asp Leu Ser Lys Leu Thr Ser Gln Ile Tyr Ile
145                 150                 155                 160
```

```
Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
    210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Val Thr Thr Ala Gly Gly Ile Thr Pro Ile Thr Ser Leu
    290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
            340

<210> SEQ ID NO 28
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 28

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Ser Pro Phe Ala Gly Gly
        35                  40                  45

Ala Ala Trp Ile Glu Gly Glu Tyr Val Pro Ala Ala Glu Ala Arg Ile
    50                  55                  60

Ser Leu Phe Asp Thr Gly Phe Gly His Ser Asp Ala Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ala Leu Ser Gln
        115                 120                 125

Leu Arg Glu Ser Phe Val Asn Ile Thr Ile Thr Arg Gly Tyr Gly Ala
    130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175
```

```
Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
    210                 215                 220

Asp Gly Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
                245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
        275                 280                 285

Leu Ile Ala Val Thr Thr Ala Gly Gly Ile Thr Pro Ile Thr Ser Leu
    290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
                325                 330                 335

Glu Ala Ile Glu Tyr
            340

<210> SEQ ID NO 29
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 29

Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Ser Pro Phe Ala Gly Gly
        35                  40                  45

Ala Ala Trp Ile Glu Gly Glu Tyr Val Pro Ala Ala Glu Ala Arg Ile
    50                  55                  60

Ser Leu Phe Asp Thr Gly Phe Gly His Ser Asp Ala Thr Tyr Ser Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Leu Gln Ser Pro Leu Thr
            100                 105                 110

Lys Ala Glu Val Glu Asp Ile Thr Lys Arg Cys Val Ser Leu Ser Gln
        115                 120                 125

Leu Arg Glu Ser Phe Val Asn Ile Thr Ile Thr Arg Gly Tyr Gly Ala
    130                 135                 140

Arg Lys Gly Glu Lys Asp Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190
```

```
Thr Val Asp Pro Thr Val Lys Asn Tyr Gln Trp Gly Asp Leu Thr Ala
        195                 200                 205

Ala Ser Phe Glu Ala Lys Asp Arg Gly Ala Arg Thr Ala Ile Leu Leu
        210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
        245                 250                 255

Ile Thr Arg Leu Thr Val Met Glu Met Ala Asp Glu Met Gly Ile Glu
        260                 265                 270

Phe Thr Leu Arg Asp Ile Thr Ser Arg Glu Leu Tyr Glu Ala Asp Glu
        275                 280                 285

Leu Ile Ala Val Thr Thr Gly Gly Ile Thr Pro Ile Thr Ser Leu
        290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Pro Ser Ser Leu Val
                    325                 330                 335

Glu Ala Ile Glu Tyr
        340
```

<210> SEQ ID NO 30
<211> LENGTH: 341
<212> TYPE: PRT
<213> ORGANISM: Unknown
<220> FEATURE:
<223> OTHER INFORMATION: Bacteria of the phylum Actinobacteria.

<400> SEQUENCE: 30

```
Met Thr Ile Ser Lys Asp Ile Asp Tyr Ser Thr Ser Asn Leu Val Ser
1               5                   10                  15

Val Ala Pro Gly Ala Ile Arg Glu Pro Thr Pro Ala Gly Ser Val Ile
            20                  25                  30

Gln Tyr Ser Asp Tyr Glu Leu Asp Glu Ser Ser Pro Phe Ala Gly Gly
        35                  40                  45

Ala Ala Trp Ile Glu Gly Glu Tyr Val Pro Ala Ala Glu Ala Arg Ile
    50                  55                  60

Ser Leu Phe Asp Thr Gly Phe Gly His Ser Asp Ala Thr Tyr Thr Val
65                  70                  75                  80

Ala His Val Trp His Gly Asn Ile Phe Arg Leu Lys Asp His Ile Asp
                85                  90                  95

Arg Val Phe Asp Gly Ala Gln Lys Leu Arg Ile Gln Ser Gln Leu Thr
            100                 105                 110

Lys Ala Glu Val Glu Asp Ile Thr Lys Arg Cys Val Ser Leu Ser Gln
        115                 120                 125

Leu Arg Glu Ser Phe Val Asn Ile Thr Ile Thr Arg Gly Tyr Gly Ala
130                 135                 140

Arg Lys Gly Glu Lys Gly Leu Ser Lys Leu Thr Ser Gln Ile Tyr Ile
145                 150                 155                 160

Tyr Ala Ile Pro Tyr Leu Trp Ala Phe Pro Pro Glu Glu Gln Ile Phe
                165                 170                 175

Gly Thr Ser Ala Ile Val Pro Arg His Val Arg Arg Ala Gly Arg Asn
            180                 185                 190

Thr Val Asp Pro Thr Val Lys Asn Tyr Gln Trp Gly Asp Leu Thr Ala
        195                 200                 205
```

Ala Ser Phe Glu Ala Lys Asp Arg Gly Ala Arg Thr Ala Ile Leu Leu
210                 215                 220

Asp Ala Asp Asn Cys Val Ala Glu Gly Pro Gly Phe Asn Val Val Met
225                 230                 235                 240

Val Lys Asp Gly Lys Leu Ser Ser Pro Ser Arg Asn Ala Leu Pro Gly
            245                 250                 255

Ile Thr Arg Leu Thr Val Met Glu Met Ala Asp Glu Met Gly Ile Glu
            260                 265                 270

Phe Thr Leu Arg Asp Ile Thr Ser Arg Glu Leu Tyr Glu Ala Asp Glu
            275                 280                 285

Leu Ile Ala Val Thr Thr Ala Gly Gly Ile Thr Pro Ile Thr Ser Leu
290                 295                 300

Asp Gly Glu Pro Leu Gly Asp Gly Thr Pro Gly Pro Val Thr Val Ala
305                 310                 315                 320

Ile Arg Asp Arg Phe Trp Ala Met Met Asp Glu Pro Ser Ser Leu Val
            325                 330                 335

Glu Ala Ile Glu Tyr
            340

<210> SEQ ID NO 31
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 31

```
atgaccatta gcaaagacat tgactatagc accagcaacc tggtgagtgt ggccccgggt     60
gcaatccgtg aacctacccc ggcaggcagc gtgatccagt acagtgacta cgagctggat    120
gaaagcagcc cgtttgccgg tggtgcagcc tggattgaag gtgagtatgt tccggcagca    180
gaggcccgta ttagcctgtt tgataccggc ttcggcccata gcgatctgac ctacaccgtt    240
gcccatgttt ggcacggcaa catctttcgc ctgaaagacc acattgaccg cgtgtttgat    300
ggcgcccaga aactgcgtct gcagagcccg ctgaccaagg ccgaagtgga ggatattacc    360
aaacgctgcg tgagcctgag tcagctgcgc gagagcttcg tgaacatcac cattacccgc    420
ggttatggcg cccgcaaagg cgagaaagat ctgagcaaat taaccagcca gatctacatc    480
tacgccatcc cgtacctgtg ggcctttcct ccggaagagc agatcttcgg tacaagtgcc    540
attgtgccgc gtcatgttcg tcgcgcaggc cgtaataccg ttgatcctac cgttaagaac    600
taccagtggg gtgatctgac cgcagcttct tttgaagcaa aagatcgtgg cgcccgcacc    660
gcaatcctgc tggatgcaga caactgtgtg gccgagggtc cgggctttaa cgtggtgatg    720
gtgaaggatg gcaaactgag tagcccgagc cgtaatgccc tgccgggtat tacacgtctg    780
accgtgatgg agatggccga tgaaatgggc atcgaattca ccctgcgcga tatcaccagc    840
cgtgagttat atgaggccga cgaactgatc gccgtgacca ccgcaggtgg cattacccccg    900
attaccagtc tggatggcga accgctgggc gatggtaccc ctggtcctgt gacagtggcc    960
attcgcgatc gcttttgggc catgatggat gagccgagca gtctggtgga ggccattgaa   1020
tattaa                                                              1026
```

<210> SEQ ID NO 32
<211> LENGTH: 1026
<212> TYPE: DNA
<213> ORGANISM: Unknown
<220> FEATURE:

<223> OTHER INFORMATION: Bacteria of the phylum Actinobacteria.

<400> SEQUENCE: 32

```
atgaccatta gcaaagacat tgactatagc accagcaacc tggtgagtgt ggccccgggt      60
gcaatccgtg aacctacccc ggcaggcagc gtgatccagt acagtgacta cgagctggat     120
gaaagcagcc cgtttgccgg tggtgcagcc tggattgaag gtgagtatgt tccggcagca     180
gaggcccgta ttagcctgtt tgataccggc ttcggccata gcgatgcgac ctacaccgtt     240
gcccatgttt ggcacggcaa catctttcgc ctgaaagacc acattgaccg cgtgtttgat     300
ggcgcccaga aactgcgtct gcagagcccg ctgaccaagg ccgaagtgga ggatattacc     360
aaacgctgcg tgagcctgag tcagctggcc gagagcttcg tgaacatcac cattacccgc     420
ggttatggcg cccgcaaagg cgagaaagat ctgagcaaat taaccagcca gatctacatc     480
tacgccatcc cgtacctgtg ggcctttcct ccggaagagc agatcttcgg tacaagtgcc     540
attgtgccgc gtcatgttcg tcgcgcaggc cgtaataccg ttgatcctac cgttaagaac     600
taccagtggg gtgatctgac cgcagcttct tttgaagcaa aagatcgtgg cgcccgcacc     660
gcaatcctgc tggatgcaga caactgtgtg gccgagggtc cgggctttaa cgtggtgatg     720
gtgaaggatg gcaaactgag tagcccgagc cgtaatgccc tgccgggtat tacacgtctg     780
accgtgatgg agatggccga tgaaatgggc atcgaattca ccctgcgcga tatcaccagc     840
cgtgagttat atgaggccga cgaactgatc gcctgcacca ccggaggtgg cattaccccg     900
attaccagtc tggatggcga accgctgggc gatggtaccc tggtcctgt gacagtggcc       960
attcgcgatc gcttttgggc catgatggat gagccgagca gtctggtgga ggccattgaa    1020
tattaa                                                               1026
```

<210> SEQ ID NO 33
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 33

```
atgaccatta gcaaagacat tgactatagc accagcaacc tggtgagtgt ggccccgggt      60
gcaatccgtg aacctacccc ggcaggcagc gtgatccagt acagtgacta cgagctggat     120
gaaagcagcc cgtttgccgg tggtgcagcc tggattgaag gtgagtatgt tccggcagca     180
gaggcccgta ttagcctgtt tgataccggc ttcggccata gcgatctgac ctacaccgtt     240
gcccatgttt ggcacggcaa catctttcgc ctgaaagacc acattgaccg cgtgtttgat     300
ggcgcccaga aactgcgtat acagagcccg ctgaccaagg ccgaagtgga ggatattacc     360
aaacgctgcg tgagcctgag tcagctgcgc gagagcttcg tgaacatcac cattacccgc     420
ggttatggcg cccgcaaagg cgagaaagat ctgagcaaat taaccagcca gatctacatc     480
tacgccatcc cgtacctgtg ggcctttcct ccggaagagc agatcttcgg tacaagtgcc     540
attgtgccgc gtcatgttcg tcgcgcaggc cgtaataccg ttgatcctac cgttaagaac     600
taccagtggg gtgatctgac cgcagcttct tttgaagcaa aagatcgtgg cgcccgcacc     660
gcaatcctgc tggatgcaga caactgtgtg gccgagggtc cgggctttaa cgtggtgatg     720
gtgaaggatg gcaaactgag tagcccgagc cgtaatgccc tgccgggtat tacacgtctg     780
accgtgatgg agatggccga tgaaatgggc atcgaattca ccctgcgcga tatcaccagc     840
cgtgagttat atgaggccga cgaactgatc gccgtgacca ccggaggtgg cattaccccg     900
```

```
attaccagtc tggatggcga accgctgggc gatggtaccc ctggtcctgt gacagtggcc      960
attcgcgatc gcttttgggc catgatggat gagccgagca gtctggtgga ggccattgaa     1020
tattaa                                                                1026

<210> SEQ ID NO 34
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 34
atgaccatta gcaaagacat tgactatagc accagcaacc tggtgagtgt ggccccgggt       60
gcaatccgtg aacctacccc ggcaggcagc gtgatccagt acagtgacta cgagctggat      120
gaaagcaacc cgtttgccgg tggtgcagcc tggattgaag gtgagtatgt tccggcagca      180
gaggcccgta ttagcctgtt tgataccggc ttcctacata gcgatctgac ctacaccgtt      240
gcccatgttt ggcacggcaa catctttcgc ctgaaagacc acattgaccg cgtgtttgat      300
ggcgcccaga aactgcgtct gcagagcccg ctgaccaagg ccgaagtgga ggatattacc      360
aaacgctgcg tgagcctgag tcagctgcgc gagagcttcg tgaacatcac cattacccgc      420
ggttatggcg cccgcaaagg cgagaaagat ctgagcaaat taccagcca gatctacatc       480 tacgccatcc cgtacctgtg ggcctttcct ccggaagagc agatcttcgg tacaagtgcc      540
attgtgccgc gtcatgttcg tcgcgcaggc cgtaataccg ttgatcctac cgttaagaac      600
taccagtggg gtgatctgac cgcagcttct tttgaagcaa agatcgtgg cgcccgcacc       660 gcaatcctgc tggatgcaga caactgtgtg ccgagggtc cgggctttaa cgtggtgatg       720
gtgaaggatg gcaaactgag tagcccgagc cgtaatgccc tgccgggtat tacacgtctg      780
accgtgatgg agatggccga tgaaatgggc atcgaattca ccctgcgcga tatcaccagc      840
cgtgagttat atgaggccga cgaactgatc gccgtgacca ccggaggtgg cattaccccg      900
attaccagtc tggatggcga accgctgggc gatggtaccc ctggtcctgt gacagtggcc      960
attcgcgatc gcttttgggc catgatggat gagccgagca gtctggtgga ggccattgaa     1020
tattaa                                                                1026

<210> SEQ ID NO 35
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 35
atgaccatta gcaaagacat tgactatagc accagcaacc tggtgagtgt ggccccgggt       60
gcaatccgtg aacctacccc ggcaggcagc gtgatccagt acagtgacta cgagctggat      120
gaaagcagcc cgtttgccgg tggtgcagcc tggattgaag gtgagtatgt tccggcagca      180
gaggcccgta ttagcctgtt tgataccggc ttcggccata gcgatctgac ctacaccgtt      240
gcccatgttt ggcacggcaa catctttcgc ctgaaagacc acattaaccg cgtgtttgat      300
ggcgcccaga tactgcgtct gcagagcccg ctgaccaagg ccgaagtgga ggatattacc      360
aaacgctgcg tgagcctgag tcagctgcgc gagagcttcg tgaacatcac cattacccgc      420
ggttatggcg cccgcaaagg cgagaaagat ctgagcaaat taccagcca gatctacatc       480
```

| | |
|---|---:|
| tacgccatcc cgtacctgtg ggcctttcct ccggaagagc agatcttcgg tacaagtgcc | 540 |
| attgtgccgc gtcatgttcg tcgcgcaggc cgtaataccg ttgatcctac cgttaagaac | 600 |
| taccagtggg gtgatctgac cgcagcttct tttgaagcaa agatcgtgg cgcccgcacc | 660 |
| gcaatcctgc tggatgcaga caactgtgtg ccgagggtc cgggctttaa cgtggtgatg | 720 |
| gtgaaggatg gcaaactgag tagcccgagc cgtaatgccc tgccgggtat tacacgtctg | 780 |
| accgtgatgg agatggccga tgaaatgggc atcgaattca ccctgcgcga tatcaccagc | 840 |
| cgtgagttat atgaggccga cgaactgatc gccgtgacca ccggaggtgg cattaccccg | 900 |
| attaccagtc tggatggcga accgctgggc gatggtaccc ctggtcctgt gacagtggcc | 960 |
| attcgcgatc gcttttgggc catgatggat gagccgagca gtctggtgga ggccattgaa | 1020 |
| tattaa | 1026 |

<210> SEQ ID NO 36
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 36

| | |
|---|---:|
| atgaccatta gcaaagacat tgactatagc accagcaacc tggtgagtgt ggccccgggt | 60 |
| gcaatccgtg aacctacccc ggcaggcagc gtgatccagt acagtgacta cgagctggat | 120 |
| gaaagcagcc cgtttgccgg tggtgcagcc tggattgaag gtgagtatgt tccggcagca | 180 |
| gaggcccgta ttagcctgtt tgataccggc ttcggccata gcgatgcgac ctacaccgtt | 240 |
| gcccatgttt ggcacggcaa catctttcgc ctgaaagacc acattgaccg cgtgtttgat | 300 |
| ggcgcccaga aactgcgtct gcagagcccg ctgaccaagg ccgaagtgga ggatattacc | 360 |
| aaacgctgcg tggccctgag tcagctgcgc gagagcttcg tgaacatcac cattacccgc | 420 |
| ggttatggcg cccgcaaagg cgagaaagat ctgagcaaat taaccagcca gatctacatc | 480 |
| tacgccatcc cgtacctgtg ggcctttcct ccggaagagc agatcttcgg tacaagtgcc | 540 |
| attgtgccgc gtcatgttcg tcgcgcaggc cgtaataccg ttgatcctac cgttaagaac | 600 |
| taccagtggg gtgatctgac cgcagcttct tttgaagcaa agatcgtgg cgcccgcacc | 660 |
| gcaatcctgc tggatgcgga caactgtgtg ccgagggtc cgggctttaa cgtggtgatg | 720 |
| gtgaaggatg gcaaactgag tagcccgagc cgtaatgccc tgccgggtat tacacgtctg | 780 |
| accgtgatgg agatggccga tgaaatgggc atcgaattca ccctgcgcga tatcaccagc | 840 |
| cgtgagttat atgaggccga cgaactgatc gccgtgacca ccggaggtgg cattaccccg | 900 |
| attaccagtc tggatggcga accgctgggc gatggtaccc ctggtcctgt gacagtggcc | 960 |
| attcgcgatc gcttttgggc catgatggat gagccgagca gtctggtgga ggccattgaa | 1020 |
| tattaa | 1026 |

<210> SEQ ID NO 37
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 37

| | |
|---|---:|
| atgaccatta gcaaagacat tgactatagc accagcaacc tggtgagtgt ggccccgggt | 60 |
| gcaatccgtg aacctacccc ggcaggcagc gtgatccagt acagtgacta cgagctggat | 120 |

```
gaaagcagcc cgtttgccgg tggtgcagcc tggattgaag gtgagtatgt tccggcagca     180
gaggcccgta ttagcctgtt tgataccggc ttcggccata cgatgcgac ctacaccgtt      240 gcccatgttt ggcacggcaa catctttcgc ctgaaagacc acattgaccg cgtgtttgat     300
ggcgcccaga aactgcgtct gcagagcccg ctgaccaagg ccgaagtgga ggatattacc     360
aaacgctgcg tggccctgag tcagctgcgc gaggccttcg tgaacatcac cattacccgc     420
ggttatggcg cccgcaaagg cgagaaagat ctgagcaaat taaccagcca gatctacatc     480
tacgccatcc cgtacctgtg ggcctttcct ccggaagagc agatcttcgg tacaagtgcc     540
attgtgccgc gtcatgttcg tcgcgcaggc cgtaataccg ttgatcctac cgttaagaac     600
taccagtggg gtgatctgac cgcagcttct tttgaagcaa agatcgtgg cgcccgcacc      660 gcaatcctgc tggatgcgga caactgtgtg gccgagggtc cgggctttaa cgtggtgatg     720
gtgaaggatg gcaaactgag tagcccgagc cgtaatgccc tgccgggtat tacacgtctg     780
accgtgatgg agatggccga tgaaatgggc atcgaattca ccctgcgcga tatcaccagc     840
cgtgagttat atgaggccga cgaactgatc gccgtgacca ccggaggtgg cattaccccg     900
attaccagtc tggatggcga accgctgggc gatggtaccc ctggtcctgt gacagtggcc     960
attcgcgatc gcttttgggc catgatggat gagccgagca gtctggtgga ggccattgaa    1020
tattaa                                                                1026

<210> SEQ ID NO 38
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 38
atgaccatta gcaaagacat tgactatagc accagcaacc tggtgagtgt ggccccgggt      60
gcaatccgtg aacctacccc ggcaggcagc gtgatccagt acagtgacta cgagctggat     120
gaaagcagcc cgtttgccgg tggtgcagcc tggattgaag gtgagtatgt tccggcagca     180
gaggcccgta ttagcctgtt tgataccggc ttcggccata cgatctgac ctacaccgtt      240 gcccatgttt ggcacggcaa catctttcgc ctgaaagacc acattgaccg cgtgtttgat     300
ggcgcccaga aactgcgtct gcagagcccg ctgaccaagg ccgaagtgga ggatattacc     360
aaacgctgcg tgagcctgag tcagctgcgc gaggccttcg tgaacatcac cattacccgc     420
ggttatggcg cccgcaaagg cgagaaagat ctgagcaaat taaccagcca gatctacatc     480
tacgccatcc cgtacctgtg ggcctttcct ccggaagagc agatcttcgg tacaagtgcc     540
attgtgccgc gtcatgttcg tcgcgcaggc cgtaataccg ttgatcctac cgttaagaac     600
taccagtggg gtgatctgac cgcagcttct tttgaagcaa agatcgtgg cgcccgcacc      660 gcaatcctgc tggatgcaga caactgtgtg gccgagggtc cgggctttaa cgtggtgatg     720
gtgaaggatg gcaaactgag tagcccgagc cgtaatgccc tgccgggtat tacacgtctg     780
accgtgatgg agatggccga tgaaatgggc atcgaattca ccctgcgcga tatcaccagc     840
cgtgagttat atgaggccga cgaactgatc gccgtgacca ccggaggtgg cattaccccg     900
attaccagtc tggatggcga accgctgggc gatggtaccc ctggtcctgt gacagtggcc     960
attcgcgatc gcttttgggc catgatggat gagccgagca gtctggtgga ggccattgaa    1020
tattaa                                                                1026
```

<210> SEQ ID NO 39
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 39

| | | | | | |
|---|---|---|---|---|---|
| atgaccatta | gcaaagacat | tgactatagc | accagcaacc | tggtgagtgt | ggccccgggt | 60 |
| gcaatccgtg | aacctacccc | ggcaggcagc | gtgatccagt | acagtgacta | cgagctggat | 120 |
| gaaagcagcc | cgtttgccgg | tggtgcagcc | tggattgaag | gtgagtatgt | tccggcagca | 180 |
| gaggcccgta | ttagcctgtt | tgataccggc | ttcctacata | gcgatctgac | ctacaccgtt | 240 |
| gcccatgttt | ggcacggcaa | catctttcgc | ctgaaagacc | acattgaccg | cgtgtttgat | 300 |
| ggcgcccaga | aactgcgtct | gcagagcccg | ctgaccaagg | ccgaagtgga | ggatattacc | 360 |
| aaacgctgcg | tgagcctgag | tcagctgcgc | gagagcttcg | tgaacatcac | cattacccgc | 420 |
| ggttatggcg | cccgcaaagg | cgagaaagat | ctgagcaaat | taaccagcca | gatctacatc | 480 |
| tacgccatcc | cgtacctgtg | ggcctttcct | ccggaagagc | agatcttcgg | tacaagtgcc | 540 |
| attgtgccgc | gtcatgttcg | tcgcgcaggc | cgtaataccg | ttgatcctac | cgttaagaac | 600 |
| taccagtggg | gtgatctgac | cgcagcttct | tttgaagcaa | agatcgtgg | cgcccgcacc | 660 |
| gcaatcctgc | tggatgcaga | caactgtgtg | gccgagggtc | cgggctttaa | cgtggtgatg | 720 |
| gtgaaggatg | gcaaactgag | tagcccgagc | cgtaatgccc | tgccgggtat | tacacgtctg | 780 |
| accgtgatga | agatggccga | tgaaatgggc | atcgaattca | ccctgcgcga | tatcaccagc | 840 |
| cgtgagttat | atgaggccga | cgaactgatc | gccgtgacca | ccggaggtgg | cattacccg | 900 |
| attaccagtc | tggatggcga | accgctgggc | gatggtaccc | ctggtcctgt | gacagtggcc | 960 |
| attcgcgatc | gcttttgggc | catgatggat | gagccgagca | gtctggtgga | ggccattgaa | 1020 |
| tattaa | | | | | | 1026 |

<210> SEQ ID NO 40
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 40

| | | | | | |
|---|---|---|---|---|---|
| atgaccatta | gcaaagacat | tgactatagc | accagcaacc | tggtgagtgt | ggccccgggt | 60 |
| gcaatccgtg | aacctacccc | ggcaggcagc | gtgatccagt | acagtgacta | cgagctggat | 120 |
| gaaagcagcc | cgtttgccgg | tggtgcagcc | tggattgaag | gtgagtatgt | tccggcagca | 180 |
| gaggcccgta | ttagcctgtt | tgataccggc | ttcctacata | gcgatctgac | ctacaccgtt | 240 |
| gcccatgttt | ggcacggcaa | catctttcgc | ctgaaagacc | acattgaccg | cgtgtttgat | 300 |
| ggcgcccaga | aactgcgtct | gcagagcccg | ctgaccaagg | ccgaagtgga | ggatattacc | 360 |
| aaacgctgcg | tgagcctgag | tcagctgcgc | gaggccttcg | tgaacatcac | cattacccgc | 420 |
| ggttatggcg | cccgcaaagg | cgagaaagat | ctgagcaaat | taaccagcca | gatctacatc | 480 |
| tacgccatcc | cgtacctgtg | ggcctttcct | ccggaagagc | agatcttcgg | tacaagtgcc | 540 |
| attgtgccgc | gtcatgttcg | tcgcgcaggc | cgtaataccg | ttgatcctac | cgttaagaac | 600 |
| taccagtggg | gtgatctgac | cgcagcttct | tttgaagcaa | agatcgtgg | cgcccgcacc | 660 |
| gcaatcctgc | tggatgcaga | caactgtgtg | gccgagggtc | cgggctttaa | cgtggtgatg | 720 |

```
gtgaaggatg gcaaactgag tagcccgagc cgtaatgccc tgccgggtat tacacgtctg    780
accgtgatgg agatggccga tgaaatgggc atcgaattca ccctgcgcga tatcaccagc    840
cgtgagttat atgaggccga cgaactgatc gccgtgacca ccggaggtgg cattaccccg    900
attaccagtc tggatggcga accgctgggc gatggtaccc tggtcctgtg acagtggcc     960 attcgcgatc gcttttgggc catgatggat gagccgagca gtctggtgga ggccattgaa   1020
tattaa                                                              1026
```

<210> SEQ ID NO 41
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 41

```
atgaccatta gcaaagacat tgactatagc accagcaacc tggtgagtgt ggccccgggt     60
gcaatccgtg aacctacccc ggcaggcagc gtgatccagt acagtgacta cgagctggat    120
gaaagcagcc cgtttgccgg tggtgcagcc tggattgaag gtgagtatgt tccggcagca    180
gaggcccgta ttagcctgtt tgataccggc ttcctacata gcgatctgac ctacaccgtt    240
gcccatgttt ggcacggcaa catctttcgc ctgaaagacc acattgaccg cgtgtttgat    300
ggcgcccaga aactgcgtct gcagagcccg ctgaccaagg ccgaagtgga ggatattacc    360
aaacgctgcg tgagcctgag tcagctcgcg gagagcttcg tgaacatcac cattacccgc    420
ggttatggcg cccgcaaagg cgagaaagat ctgagcaaat taaccagcca gatctacatc    480
tacgccatcc cgtacctgtg gcctttcct ccggaagagc agatcttcgg tacaagtgcc    540
attgtgccgc gtcatgttcg tcgcgcaggc cgtaataccg ttgatcctac cgttaagaac    600
taccagtggg gtgatctgac cgcagcttct tttgaagcaa agatcgtgg cgcccgcacc    660 gcaatcctgc tggatgcaga caactgtgtg gccgagggtc cgggctttaa cgtggtgatg    720
gtgaaggatg gcaaactgag tagcccgagc cgtaatgccc tgccgggtat tacacgtctg    780
accgtgatgg agatggccga tgaaatgggc atcgaattca ccctgcgcga tatcaccagc    840
cgtgagttat atgaggccga cgaactgatc gcctgcacca ccggaggtgg cattaccccg    900
attaccagtc tggatggcga accgctgggc gatggtaccc tggtcctgtg acagtggcc     960 attcgcgatc gcttttgggc catgatggat gagccgagca gtctggtgga ggccattgaa   1020
tattaa                                                              1026
```

<210> SEQ ID NO 42
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 42

```
atgaccatta gcaaagacat tgactatagc accagcaacc tggtgagtgt ggccccgggt     60
gcaatccgtg aacctacccc ggcaggcagc gtgatccagt acagtgacta cgagctggat    120
gaaagcagcc cgtttgccgg tggtgcagcc tggattgaag gtgagtatgt tccggcagca    180
gaggcccgta ttagcctgtt tgataccggc ttcctacata gcgatgcgac ctacaccgtt    240
gcccatgttt ggcacggcaa catctttcgc ctgaaagacc acattgaccg cgtgtttgat    300
```

```
ggcgcccaga aactgcgtct gcagagcccg ctgaccaagg ccgaagtgga ggatattacc    360
aaacgctgcg tgagcctgag tcagctgcgc gagagcttcg tgaacatcac cattacccgc    420
ggttatggcg cccgcaaagg cgagaaagat ctgagcaaat taaccagcca gatctacatc    480
tacgccatcc cgtacctgtg ggcctttcct ccggaagagc agatcttcgg tacaagtgcc    540
attgtgccgc gtcatgttcg tcgcgcaggc cgtaataccg ttgatcctac cgttaagaac    600
taccagtggg gtgatctgac cgcagcttct tttgaagcaa agatcgtgg cgcccgcacc     660 gcaatcctgc tggatgcaga caactgtgtg gccgagggtc cgggctttaa cgtggtgatg    720
gtgaaggatg gcaaactgag tagcccgagc cgtaatgccc tgccgggtat tacacgtctg    780
accgtgatgg agatggccga tgaaatgggc atcgaattca ccctgcgcga tatcaccagc    840
cgtgagttat atgaggccga cgaactgatc gcctgcacca ccggaggtgg cattaccccg    900
attaccagtc tggatggcga accgctgggc gatggtaccc ctggtcctgt gacagtggcc    960
attcgcgatc gcttttgggc catgatggat gagccgagca gtctggtgga ggccattgaa   1020
tattaa                                                              1026

<210> SEQ ID NO 43
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 43
atgaccatta gcaaagacat tgactatagc accagcaacc tggtgagtgt ggccccgggt     60
gcaatccgtg aacctacccc ggcaggcagc gtgatccagt acagtgacta cgagctggat    120
gaaagcagcc cgtttgccgg tggtgcagcc tggattgaag gtgagtatgt tccggcagca    180
gaggcccgta ttagcctgtt tgataccggc ttcctacata gcgatctgac ctacaccgtt    240
gcccatgttt ggcacggcaa catctttcgc ctgaaagacc acattgaccg cgtgtttgat    300
ggcgcccaga aactgcgtct gcagagcccg ctgaccaagg ccgaagtgga ggatattacc    360
aaacgctgcg tgagcctgag tcagctgcgc gagagcttcg tgaacatcac cattacccgc    420
ggttatggcg cccgcaaagg cgagaaagat ctgagcaaat taaccagcca gatctacatc    480
tacgccatcc cgtacctgtg ggcctttcct ccggaagagc agatcttcgg tacaagtgcc    540
attgtgccgc gtcatgttcg tcgcgcaggc cgtaataccg ttgatcctac cgttaagaac    600
taccagtggg gtgatctgac cgcagcttct tttgaagcaa agatcgtgg cgcccgcacc     660 gcaatcctgc tggatgcaga caactgtgtg gccgagggtc cgggctttaa cgtggtgatg    720
gtgaaggatg gcaaactgag tagcccgagc cgtaatgccc tgccgggtat tacacgtctg    780
accgtgatgg agatggccga tgaaatgggc atcgaattca ccctgcgcga tatcaccagc    840
cgtgagttat atgaggccga cgaactgatc gccgtgacca ccgcaggtgg cattaccccg    900
attaccagtc tggatggcga accgctgggc gatggtaccc ctggtcctgt gacagtggcc    960
attcgcgatc gcttttgggc catgatggat gagccgagca gtctggtgga ggccattgaa   1020
tattaa                                                              1026

<210> SEQ ID NO 44
<211> LENGTH: 1026
<212> TYPE: DNA
<213> ORGANISM: Unknown
<220> FEATURE:
<223> OTHER INFORMATION: Bacteria of the phylum Actinobacteria.
```

<400> SEQUENCE: 44

```
atgaccatta gcaaagacat tgactatagc accagcaacc tggtgagtgt ggccccgggt      60
gcaatccgtg aacctacccc ggcaggcagc gtgatccagt acagtgacta cgagctggat     120
gaaagcagcc cgtttgccgg tggtgcagcc tggattgaag gtgagtatgt tccggcagca     180
gaggcccgta ttagcctgtt tgataccggc ttcggccata gcgatgcgac ctacaccgtt     240
gcccatgttt ggcacggcaa catctttcgc ctgaaagacc acattgaccg cgtgtttgat     300
ggcgcccaga aactgcgtct gcagagcccg ctgaccaagg ccgaagtgga ggatattacc     360
aaacgctgcg tgagcctgag tcagctgcgc gagagcttcg tgaacatcac cattacccgc     420
ggttatggcg cccgcaaagg cgagaaagat ctgagcaaat taaccagcca gatctacatc     480
tacgccatcc cgtacctgtg gccctttcct ccggaagagc agatcttcgg tacaagtgcc     540
attgtgccgc gtcatgttcg tcgcgcaggc cgtaataccg ttgatcctac cgttaagaac     600
taccagtggg gtgatctgac cgcagcttct tttgaagcaa aagatcgtgg cgcccgcacc     660
gcaatcctgc tggatgcaga caactgtgtg gccgagggtc cgggctttaa cgtggtgatg     720
gtgaaggatg gcaaactgag tagcccgagc cgtaatgccc tgccgggtat tacacgtctg     780
accgtgatgg agatggccga tgaaatgggc atcgaattca ccctgcgcga tatcaccagc     840
cgtgagttat atgaggccga cgaactgatc gccgtgacca ccgcaggtgg cattaccccg     900
attaccagtc tggatggcga accgctgggc gatggtaccc ctggtcctgt gacagtggcc     960
attcgcgatc gcttttgggc catgatggat gagccgagca gtctggtgga ggccattgaa    1020
tattaa                                                               1026
```

<210> SEQ ID NO 45
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 45

```
atgaccatta gcaaagacat tgactatagc accagcaacc tggtgagtgt ggccccgggt      60
gcaatccgtg aacctacccc ggcaggcagc gtgatccagt acagtgacta cgagctggat     120
gaaagcagcc cgtttgccgg tggtgcagcc tggattgaag gtgagtatgt tccggcagca     180
gaggcccgta ttagcctgtt tgataccggc ttcggccata gcgatctgac ctacaccgtt     240
gcccatgttt ggcacggcaa catctttcgc ctgaaagacc acattgaccg cgtgtttgat     300
ggcgcccaga aactgcgtat acagagcccg ctgaccaagg ccgaagtgga ggatattacc     360
aaacgctgcg tgagcctgag tcagctgcgc gagagcttcg tgaacatcac cattacccgc     420
ggttatggcg cccgcaaagg cgagaaagat ctgagcaaat taaccagcca gatctacatc     480
tacgccatcc cgtacctgtg gccctttcct ccggaagagc agatcttcgg tacaagtgcc     540
attgtgccgc gtcatgttcg tcgcgcaggc cgtaataccg ttgatcctac cgttaagaac     600
taccagtggg gtgatctgac cgcagcttct tttgaagcaa aagatcgtgg cgcccgcacc     660
gcaatcctgc tggatgcaga caactgtgtg gccgagggtc cgggctttaa cgtggtgatg     720
gtgaaggatg gcaaactgag tagcccgagc cgtaatgccc tgccgggtat tacacgtctg     780
accgtgatgg agatggccga tgaaatgggc atcgaattca ccctgcgcga tatcaccagc     840
cgtgagttat atgaggccga cgaactgatc gccgtgacca ccgcaggtgg cattaccccg     900
```

| | |
|---|---|
| attaccagtc tggatggcga accgctgggc gatggtaccc ctggtcctgt gacagtggcc | 960 |
| attcgcgatc gcttttgggc catgatggat gagccgagca gtctggtgga ggccattgaa | 1020 |
| tattaa | 1026 |

<210> SEQ ID NO 46
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 46

| | |
|---|---|
| atgaccatta gcaaagacat tgactatagc accagcaacc tggtgagtgt ggccccgggt | 60 |
| gcaatccgtg aacctacccc ggcaggcagc gtgatccagt acagtgacta cgagctggat | 120 |
| gaaagcagcc cgtttgccgg tggtgcagcc tggattgaag gtgagtatgt tccggcagca | 180 |
| gaggcccgta ttagcctgtt tgataccggc ttcggccata gcgatctgac ctacaccgtt | 240 |
| gcccatgttt ggcacggcaa catctttcgc ctgggagacc acattgaccg cgtgtttgat | 300 |
| ggcgcccaga actgcgtct gcagagcccg ctgaccaagg ccgaagtgga ggatattacc | 360 |
| aaacgctgcg tgagcctgag tcagctgcgc gagagcttcg tgaacatcac cattacccgc | 420 |
| ggttatggcg cccgcaaagg cgagaaagat ctgagcaaat taaccagcca gatctacatc | 480 |
| tacgccatcc cgtacctgtg ggcctttcct ccggaagagc agatcttcgg tacaagtgcc | 540 |
| attgtgccgc gtcatgttcg tcgcgcaggc cgtaataccg ttgatcctac cgttaagaac | 600 |
| taccagtggg gtgatctgac cgcagcttct tttgaagcaa aagatcgtgg cgcccgcacc | 660 |
| gcaatcctgc tggatgcaga caactgtgtg gccgagggtc cgggctttaa cgtggtgatg | 720 |
| gtgaaggatg gcaaactgag tagcccgagc cgtaatgccc tgccgggtat tacacgtctg | 780 |
| accgtgatgg agatggccga tgaaatgggc atcgaattca ccctgcgcga tatcaccagc | 840 |
| cgtgagttat atgaggccga cgaactgatc gccgtgacca ccgcaggtgg cattaccccg | 900 |
| attaccagtc tggatggcga accgctgggc gatggtaccc ctggtcctgt gacagtggcc | 960 |
| attcgcgatc gcttttgggc catgatggat gagccgagca gtctggtgga ggccattgaa | 1020 |
| tattaa | 1026 |

<210> SEQ ID NO 47
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 47

| | |
|---|---|
| atgaccatta gcaaagacat tgactatagc accagcaacc tggtgagtgt ggccccgggt | 60 |
| gcaatccgtg aacctacccc ggcaggcagc gtgatccagt acagtgacta cgagctggat | 120 |
| gaaagcagcc cgtttgccgg tggtgcagcc tggattgaag gtgagtatgt tccggcagca | 180 |
| gaggcccgta ttagcctgtt tgataccggc ttcggccata gcgatctgac ctacaccgtt | 240 |
| gcccatgttt ggcacggcaa catctttcgc ctgaaagacc acattgaccg cgtgtttgat | 300 |
| ggcgcccaga actgcgtct gcagagcccg ctgaccaagg ccgaagtgga ggatattacc | 360 |
| aaacgctgcg tggccctgag tcagctgcgc gagagcttcg tgaacatcac cattacccgc | 420 |
| ggttatggcg cccgcaaagg cgagaaagat ctgagcaaat taaccagcca gatctacatc | 480 |
| tacgccatcc cgtacctgtg ggcctttcct ccggaagagc agatcttcgg tacaagtgcc | 540 |

| | |
|---|---|
| attgtgccgc gtcatgttcg tcgcgcaggc cgtaataccg ttgatcctac cgttaagaac | 600 |
| taccagtggg gtgatctgac cgcagcttct tttgaagcaa aagatcgtgg cgcccgcacc | 660 |
| gcaatcctgc tggatgcaga caactgtgtg gccgagggtc cgggctttaa cgtggtgatg | 720 |
| gtgaaggatg gcaaactgag tagcccgagc cgtaatgccc tgccgggtat tacacgtctg | 780 |
| accgtgatgg agatggccga tgaaatgggc atcgaattca ccctgcgcga tatcaccagc | 840 |
| cgtgagttat atgaggccga cgaactgatc gccgtgacca ccgcaggtgg cattaccccg | 900 |
| attaccagtc tggatggcga accgctgggc gatggtaccc ctggtcctgt gacagtggcc | 960 |
| attcgcgatc gcttttgggc catgatggat gagcccgagc gtctggtgga ggccattgaa | 1020 |
| tattaa | 1026 |

<210> SEQ ID NO 48
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 48

| | |
|---|---|
| atgaccatta gcaaagacat tgactatagc accagcaacc tggtgagtgt ggccccgggt | 60 |
| gcaatccgtg aacctacccc ggcaggcagc gtgatccagt acagtgacta cgagctggat | 120 |
| gaaagcagcc cgtttgccgg tggtgcagcc tggattgaag gtgagtatgt tccggcagca | 180 |
| gaggcccgta ttagcctgtt tgataccggc ttcggcccata gcgatctgac ctacaccgtt | 240 |
| gcccatgttt ggcacggcaa catctttcgc ctgaaagacc acattgaccg cgtgtttgat | 300 |
| ggcgcccaga actgcgtcct gcagagcccg ctgaccaagg ccgaagtgga ggatattacc | 360 |
| aaacgctgcg tgagcctgag tcagctgcgc gaggccttcg tgaacatcac cattacccgc | 420 |
| ggttatggcg cccgcaaagg cgagaaagat ctgagcaaat taaccagcca gatctacatc | 480 |
| tacgccatcc cgtacctgtg ggcctttcct ccggaagagc agatcttcgg tacaagtgcc | 540 |
| attgtgccgc gtcatgttcg tcgcgcaggc cgtaataccg ttgatcctac cgttaagaac | 600 |
| taccagtggg gtgatctgac cgcagcttct tttgaagcaa aagatcgtgg cgcccgcacc | 660 |
| gcaatcctgc tggatgcaga caactgtgtg gccgagggtc cgggctttaa cgtggtgatg | 720 |
| gtgaaggatg gcaaactgag tagcccgagc cgtaatgccc tgccgggtat tacacgtctg | 780 |
| accgtgatgg agatggccga tgaaatgggc atcgaattca ccctgcgcga tatcaccagc | 840 |
| cgtgagttat atgaggccga cgaactgatc gccgtgacca ccgcaggtgg cattaccccg | 900 |
| attaccagtc tggatggcga accgctgggc gatggtaccc ctggtcctgt gacagtggcc | 960 |
| attcgcgatc gcttttgggc catgatggat gagcccgagc gtctggtgga ggccattgaa | 1020 |
| tattaa | 1026 |

<210> SEQ ID NO 49
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 49

| | |
|---|---|
| atgaccatta gcaaagacat tgactatagc accagcaacc tggtgagtgt ggccccgggt | 60 |
| gcaatccgtg aacctacccc ggcaggcagc gtgatccagt acagtgacta cgagctggat | 120 |

```
gaaagcagcc cgtttgccgg tggtgcagcc tggattgaag gtgagtatgt tccggcagca      180
gaggcccgta ttagcctgtt tgataccggc ttcggccata cgatctgac ctacaccgtt       240 gcccatgttt ggcacggcaa catctttcgc ctgaaagacc acattgaccg cgtgtttgat      300
ggcgcccaga aactgcgtct gcagagcccg ctgaccaagg ccgaagtgga ggatattacc     360
aaacgctgcg tgagcctgag tcagctgcgc gagagcttcg tgaacatcac cattacccgc     420
ggttatggcg cccgcaaagg cgagaaagat ctgagcaaat taaccagcca gatctacatc    480
tacgccatcc cgtacctgtg ggcctttcct ccggaagagc agatcttcgg tacaagtgcc   540
attgtgccgc gtcatgttcg tcgcgcaggc cgtaataccg ttgatcctac cgttaagaac    600
taccagtggg gtgatctgac cgcagcttct tttgaagcaa agatcgtgg cgcccgcacc     660 gcaatcctgc tggatggaga caactgtgtg gccgagggtc cgggctttaa cgtggtgatg   720
gtgaaggatg gcaaactgag tagcccgagc cgtaatgccc tgccgggtat tacacgtctg    780
accgtgatgg agatggccga tgaaatgggc atcgaattca ccctgcgcga tatcaccagc    840
cgtgagttat atgaggccga cgaactgatc gccgtgacca ccgcaggtgg cattaccccg     900
attaccagtc tggatggcga accgctgggc gatggtaccc ctggtcctgt gacagtggcc    960
attcgcgatc gcttttgggc catgatggat gagccgagca gtctggtgga ggccattgaa    1020
tattaa                                                                1026

<210> SEQ ID NO 50
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 50
atgaccatta gcaaagacat tgactatagc accagcaacc tggtgagtgt ggccccgggt       60
gcaatccgtg aacctacccc ggcaggcagc gtgatccagt acagtgacta cgagctggat     120
gaaagcagcc cgtttgccgg tggtgcagcc tggattgaag gtgagtatgt tccggcagca   180
gaggcccgta ttagcctgtt tgataccggc ttcggccata cgatctgac ctacaccgtt     240 gcccatgttt ggcacggcaa catctttcgc ctgaaagacc acattgaccg cgtgtttgat    300
ggcgcccaga aactgcgtct gcagagcccg ctgaccaagg ccgaagtgga ggatattacc    360
aaacgctgcg tgagcctgag tcagctgcgc gagagcttcg tgaacatcac cattacccgc     420
ggttatggcg cccgcaaagg cgagaaagat ctgagcaaat taaccagcca gatctacatc   480
tacgccatcc cgtacctgtg ggcctttcct ccggaagagc agatcttcgg tacaagtgcc    540
attgtgccgc gtcatgttcg tcgcgcaggc cgtaataccg ttgatcctac cgttaagaac    600
taccagtggg gtgatctgac cgcagcttct tttgaagcaa agatcgtgg cgcccgcacc    660 gcaatcctgc tggatgcaga caactgtgtg gccgagggtc cgggctttaa cgtggtgatg    720
gtgaaggatg gcaaactgag tagcccgagc cgtaatgccc tgccgggtat tacacgtctg    780
accgtgatgg agatggccga tgaaatgggc atcgaattca ccctgcgcga tatcaccagc    840
cgtgagttat atgaggccga cgaactgatc gcctgcacca ccgcaggtgg cattaccccg    900
attaccagtc tggatggcga accgctgggc gatggtaccc ctggtcctgt gacagtggcc   960
attcgcgatc gcttttgggc catgatggat gagccgagca gtctggtgga ggccattgaa    1020
tattaa                                                                1026
```

<210> SEQ ID NO 51
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 51

| | |
|---|---|
| atgaccatta gcaaagacat tgactatagc accagcaacc tggtgagtgt ggccccgggt | 60 |
| gcaatccgtg aacctacccc ggcaggcagc gtgatccagt acagtgacta cgagctggat | 120 |
| gaaagcagcc cgtttgccgg tggtgcagcc tggattgaag gtgagtatgt tccggcagca | 180 |
| gaggcccgta ttagcctgtt tgataccggc ttcggccata gcgatctgac ctacaccgtt | 240 |
| gcccatgttt ggcacggcaa catctttcgc ctgaaagacc acattgaccg cgtgtttgat | 300 |
| ggcgcccaga aactgcgtct gcagagcccg ctgaccaagg ccgaagtgga ggatattacc | 360 |
| aaacgctgcg tgagcctgag tcagctgcgc gagagcttcg tgaacatcac cattacccgc | 420 |
| ggttatggcg cccgcaaagg cgagaaagat ctgagcaaat taaccagcca gatctacatc | 480 |
| tacgccatcc cgtacctgtg ggcctttcct ccggaagagc agatcttcgg tacaagtgcc | 540 |
| attgtgccgc gtcatgttcg tcgcgcaggc cgtaataccg ttgatcctac cgttaagaac | 600 |
| taccagtggg gtgatctgac cgcagcttct tttgaagcaa agatcgtgg cgcccgcacc | 660 |
| gcaatcctgc tggatgcaga caactgtgtg gccgagggtc cgggctttaa cgtggtgatg | 720 |
| gtgaaggatg gcaaactgag tagcccgagc cgtaatgccc tgccgggtat tacacgtctg | 780 |
| accgtgatgg agatggccga tgaaatgggc atcgaattca ccctgcgcga tatcaccagc | 840 |
| cgtgagttat atgaggccga cgaactgatc gccgtgacca ccggaggtgg cattacccccg | 900 |
| attaccagtc tggatggcga accgctgggc gatggtaccc ctggtcctgt gacagtggcc | 960 |
| attcgcgatc gcttttgggc catgatggat gagccgagca gtctggtgga ggccattgaa | 1020 |
| tattaa | 1026 |

<210> SEQ ID NO 52
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 52

| | |
|---|---|
| atgaccatta gcaaagacat tgactatagc accagcaacc tggtgagtgt ggcctcgggt | 60 |
| gcaatccgtg aacctacccc ggcaggcagc gtgatccagt acagtgacta cgagctggat | 120 |
| gaaagcagcc cgtttgccgg tggtgcagcc tggattgaag gtgagtatgt tccggcagca | 180 |
| gaggcccgta ttagcctgtt tgataccggc ttcggccata gcgatctgac ctacaccgtt | 240 |
| gcccatgttt ggcacggcaa catctttcgc ctgaaagacc acattgaccg cgtgtttgat | 300 |
| ggcgcccaga aactgcgtct gcagagcccg ctgaccaagg ccgaagtgga ggatattacc | 360 |
| aaacgctgcg tgagcctgag tcagctgcgc gagagcttcg tgaacatcac cattacccgc | 420 |
| ggttatggcg cccgcaaagg cgagaaagat ctgagcaaat taaccagcca gatctacatc | 480 |
| tacgccatcc cgtacctgtg ggcctttcct ccggaagagc agatcttcgg tacaagtgcc | 540 |
| attgtgccgc gtcatgttcg tcgcgcaggc cgtaataccg ttgatcctac cgttaagaac | 600 |
| taccagtggg gtgatctgac cgcagcttct tttgaagcaa agatcgtgg cgcccgcacc | 660 |
| gcaatcctgc tggatgcaga caactgtgtg gccgagggtc cgggctttaa cgtggtgatg | 720 |

```
gtgaaggatg gcaaactgag tagcccgagc cgtaatgccc tgccgggtat tacacgtctg      780
accgtgatgg agatggccga tgaaatgggc atcgaattca ccctgcgcga tatcaccagc      840
cgtgagttat atgaggccga cgaactgatc gccgtgacca ccgcaggtgg cattaccccg      900
attaccagtc tggatggcga accgctgggc gatggtaccc ctggtcctgt gacagtggcc      960
attcgcgatc gcttttgggc catgatggat gagccgagca gtctggtgga ggccattgaa     1020
tattaa                                                                1026

<210> SEQ ID NO 53
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 53
atgaccatta gcaaagacat tgactatagc accagcaacc tggtgagtgt ggccccgggt       60
gcaatccgtg aacctacccc ggcaggcagc gtgatccagt acagtgacta cgagctggat      120
tcaagcagcc cgtttgccgg tggtgcagcc tggattgaag gtgagtatgt tccggcagca      180
gaggcccgta ttagcctgtt tgataccggc ttcggccata gcgatctgac ctacaccgtt      240
gcccatgttt ggcacggcaa catctttcgc ctgaaagacc acattgaccg cgtgtttgat      300
ggcgcccaga aactgcgtct gcagagcccg ctgaccaagg ccgaagtgga ggatattacc      360
aaacgctgcg tgagcctgag tcagctgcgc gagagcttcg tgaacatcac cattacccgc      420
ggttatggcg cccgcaaagg cgagaaagat ctgagcaaat taaccagcca gatctacatc      480
tacgccatcc cgtacctgtg ggcctttcct ccggaagagc agatcttcgg tacaagtgcc      540
attgtgccgc gtcatgttcg tcgcgcaggc cgtaataccg ttgatcctac cgttaagaac      600
taccagtggg gtgatctgac cgcagcttct tttgaagcaa agatcgtgg cgcccgcacc       660 gcaatcctgc tggatgcaga caactgtgtg gccgagggtc cgggctttaa cgtggtgatg      720
gtgaaggatg gcaaactgag tagcccgagc cgtaatgccc tgccgggtat tacacgtctg      780
accgtgatgg agatggccga tgaaatgggc atcgaattca ccctgcgcga tatcaccagc      840
cgtgagttat atgaggccga cgaactgatc gccgtgacca ccgcaggtgg cattaccccg      900
attaccagtc tggatggcga accgctgggc gatggtaccc ctggtcctgt gacagtggcc      960
attcgcgatc gcttttgggc catgatggat gagccgagca gtctggtgga ggccattgaa     1020
tattaa                                                                1026

<210> SEQ ID NO 54
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 54
atgaccatta gcaaagacat tgactatagc accagcaacc tggtgagtgt ggccccgggt       60
gcaatccgtg aacctacccc ggcaggcagc gtgatccagt acagtgacta cgagctggat      120
gaaagcaacc cgtttgccgg tggtgcagcc tggattgaag gtgagtatgt tccggcagca      180
gaggcccgta ttagcctgtt tgataccggc ttcggccata gcgatctgac ctacaccgtt      240
gcccatgttt ggcacggcaa catctttcgc ctgaaagacc acattgaccg cgtgtttgat      300
ggcgcccaga aactgcgtct gcagagcccg ctgaccaagg ccgaagtgga ggatattacc      360
```

-continued

```
aaacgctgcg tgagcctgag tcagctgcgc gagagcttcg tgaacatcac cattacccgc    420
ggttatggcg cccgcaaagg cgagaaagat ctgagcaaat taaccagcca gatctacatc    480
tacgccatcc cgtacctgtg ggcctttcct ccggaagagc agatcttcgg tacaagtgcc    540
attgtgccgc gtcatgttcg tcgcgcaggc cgtaataccg ttgatcctac cgttaagaac    600
taccagtggg gtgatctgac cgcagcttct tttgaagcaa agatcgtggc gcccgcacc    660 gcaatcctgc tggatgcaga caactgtgtg gccgagggtc cgggctttaa cgtggtgatg    720
gtgaaggatg gcaaactgag tagcccgagc cgtaatgccc tgccgggtat tacacgtctg    780
accgtgatgg agatggccga tgaaatgggc atcgaattca ccctgcgcga tatcaccagc    840
cgtgagttat atgaggccga cgaactgatc gccgtgacca ccgcaggtgg cattaccccg    900
attaccagtc tggatggcga accgctgggc gatggtaccc ctggtcctgt gacagtggcc    960
attcgcgatc gcttttgggc catgatggat gagccgagca gtctggtgga ggccattgaa   1020
tattaa                                                              1026

<210> SEQ ID NO 55
<211> LENGTH: 935
<212> TYPE: DNA
<213> ORGANISM: Unknown
<220> FEATURE:
<223> OTHER INFORMATION: Bacteria of the phylum Actinobacteria.

<400> SEQUENCE: 55
tgatccagta cagtgactac gagctggatg aaagcagccc gtttgccggt ggtgcagcct     60
ggattgaagg tgagtatgtt ccggcagcag aggcccgtat tagcctgttt gataccggct    120
tcggccatag cgatctgacc tacaccgttg cccatgtttg gcacggcaac atctttcgcc    180
tgaaagacca cattgaccgc gtgtttgatg gcgcccagaa actgcgtctg cagagcccgc    240
tgaccaaggc cgaagtggag gatattacca aacgctgcgt gagcctgagt cagctgcgcg    300
agagcttcgt gaacatcacc attacccgcg ttatggcgc ccgcaaaggc gagaaagatc    360
tgagcaaatt aaccagccag atctacatct acgccatccc gtacctgtgg gcctttcctc    420
cggaagagca gatcttcggt acaagtgcca ttgtgccgcg tcatgttcgt cgcgcaggcc    480
gtaataccgt tgatcctacc gttaagaact accagtgggg tgatctgacc gcagcttctt    540
ttgaagcaaa agatcgtggc gcccgcaccg caatcctgct ggatgcagac aactgtgtgg    600
ccgagggtcc gggctttaac gtggtgatgg tgaaggatgg caaactgagt agcccgagcc    660
gtaatgccct gccgggtatt acacgtctga ccgtgatgga gatggccgat gaaatgggca    720
tcgaattcac cctgcgcgat atcaccagcc gtgagttata tgaggccgac gaactgatcg    780
ccgtgaccac cgcaggtggc attacccccga ttaccagtct ggatggcgaa ccgctgggcg    840
atggtacccc tggtcctgtg acagtggcca ttcgcgatcg cttttgggcc atgatggatg    900
agccgagcag tctggtggag gccattgaat attaa                               935

<210> SEQ ID NO 56
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 56
atgaccatta gcaaagacat tgactatagc accagcaacc tggtgagtgt ggccccgggt     60
```

```
gcaatccgtg aacctacccc ggcaggcagc gtgatccagt acagtgacta cgagctggat      120
gaaagcagcc cgtttgccgg tggtgcagcc tggattgaag gtgagtatgt tccggcagca      180
gaggcccgta ttagcctgtt tgataccggc ttcggccata gcgatctgac ctacaccgtt      240
gcccatgttt ggcacggcaa catctttcgc ctgaaagacc acattgaccg cgtgtttgat      300
ggcgcccaga aactgcgtct gcagagcccg ctgaccaagg ccgaagtgga ggatattacc      360
aaacgctgcg tgagcctgag tcagctgcgc gagagcttcg tgaacatcac cattacccgc      420
ggttatggcg cccgcaaagg cgagaaagat ctgagcaaat taaccagcca gatctacatc      480
tacgccatcc cgtacctgtg gcctttcct ccggaagagc agatcttcgg tacaagtgcc      540
attgtgccgc gtcatgttcg tcgcgcaggc cgtaataccg ttgatcctac cgttaagaac      600
taccagtggg gtgatctgac cgcagcttct tttgaagcaa agatcgtgg cgcccgcacc      660 gcaatcctgc tggatgcaga caactgtgtg gccgagggtc cgggctttaa cgtggtgatg      720
gtgaaggatg gcaaactgag tagcccgagc cgtaatgccc tgccgggtat tacacgtctg      780
accgtgatgg agatggccga tgaaatgggc atcgaattca ccctgcgcga tatcaccagc      840
cgtgagttat atgaggccga cgaactgatc gccgtgacca ccgcaggtgg cattaccccg      900
attaccagtc tggatggcga accgctgggc gatggtaccc tggtcctgt gacagtggcc      960 attcgcgatc gcttttgggc catgatggat gagtcgagca gtctggtgga ggccattgaa     1020
tattaa                                                                 1026

<210> SEQ ID NO 57
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 57
atgaccatta gcaaagacat tgactatagc accagcaacc tggtgagtgt ggccccgggt       60
gcaatccgtg aacctacccc ggcaggcagc gtgatccagt acagtgacta cgagctggat      120
gaaagcagcc cgtttgccgg tggtgcagcc tggattgaag gtgagtatgt tccggcagca      180
gaggcccgta ttagcctgtt tgataccggc ttcggccata gcgatgcgac ctacaccgtt      240
gcccatgttt ggcacggcaa catctttcgc ctgaaagacc acattgaccg cgtgtttgat      300
ggcgcccaga aactgcgtat acagagccag ctgaccaagg ccgaagtgga ggatattacc      360
aaacgctgcg tgagcctgag tcagctgcgc gagagcttcg tgaacatcac cattacccgc      420
ggttatggcg cccgcaaagg cgagaaagat ctgagcaaat taaccagcca gatctacatc      480
tacgccatcc cgtacctgtg gcctttcct ccggaagagc agatcttcgg tacaagtgcc      540
attgtgccgc gtcatgttcg tcgcgcaggc cgtaataccg ttgatcctac cgttaagaac      600
taccagtggg gtgatctgac cgcagcttct tttgaagcaa agatcgtgg cgcccgcacc      660 gcaatcctgc tggatgcaga caactgtgtg gccgagggtc cgggctttaa cgtggtgatg      720
gtgaaggatg gcaaactgag tagcccgagc cgtaatgccc tgccgggtat tacacgtctg      780
accgtgatgg agatggccga tgaaatgggc atcgaattca ccctgcgcga tatcaccagc      840
cgtgagttat atgaggccga cgaactgatc gccgtgacca ccgcaggtgg cattaccccg      900
attaccagtc tggatggcga accgctgggc gatggtaccc tggtcctgt gacagtggcc      960 attcgcgatc gcttttgggc catgatggat gagccgagca gtctggtgga ggccattgaa     1020
tattaa                                                                 1026
```

<210> SEQ ID NO 58
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 58

| | |
|---|---|
| atgaccatta gcaaagacat tgactatagc accagcaacc tggtgagtgt ggccccgggt | 60 |
| gcaatccgtg aacctacccc ggcaggcagc gtgatccagt acagtgacta cgagctggat | 120 |
| gaaagcagcc cgtttgccgg tggtgcagcc tggattgaag gtgagtatgt tccggcagca | 180 |
| gaggcccgta ttagcctgtt tgataccggc ttcggccata gcgatgcgac ctacaccgtt | 240 |
| gcccatgttt ggcacggcaa catctttcgc ctgaaagacc acattgaccg cgtgtttgat | 300 |
| ggcgcccaga aactgcgtct gcagagcccg ctgaccaagg ccgaagtgga ggatattacc | 360 |
| aaacgctgcg tggccctgag tcagctgcgc gagagcttcg tgaacatcac cattacccgc | 420 |
| ggttatggcg cccgcaaagg cgagaaagat ctgagcaaat taaccagcca gatctacatc | 480 |
| tacgccatcc cgtacctgtg ggcctttcct ccggaagagc agatcttcgg tacaagtgcc | 540 |
| attgtgccgc gtcatgttcg tcgcgcaggc cgtaataccg ttgatcctac cgttaagaac | 600 |
| taccagtggg gtgatctgac cgcagcttct tttgaagcaa aagatcgtgg cgcccgcacc | 660 |
| gcaatcctgc tggatggaga caactgtgtg gccgagggtc cgggctttaa cgtggtgatg | 720 |
| gtgaaggatg gcaaactgag tagcccgagc cgtaatgccc tgccgggtat tacacgtctg | 780 |
| accgtgatgg agatggccga tgaaatgggc atcgaattca ccctgcgcga tatcaccagc | 840 |
| cgtgagttat atgaggccga cgaactgatc gccgtgacca ccgcaggtgg cattaccccg | 900 |
| attaccagtc tggatggcga accgctgggc gatggtaccc ctggtcctgt gacagtggcc | 960 |
| attcgcgatc gcttttgggc catgatggat gagccgagca gtctggtgga ggccattgaa | 1020 |
| tattaa | 1026 |

<210> SEQ ID NO 59
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 59

| | |
|---|---|
| atgaccatta gcaaagacat tgactatagc accagcaacc tggtgagtgt ggccccgggt | 60 |
| gcaatccgtg aacctacccc ggcaggcagc gtgatccagt acagtgacta cgagctggat | 120 |
| gaaagcagcc cgtttgccgg tggtgcagcc tggattgaag gtgagtatgt tccggcagca | 180 |
| gaggcccgta ttagcctgtt tgataccggc ttcggccata gcgatgcgac ctacagcgtt | 240 |
| gcccatgttt ggcacggcaa catctttcgc ctgaaagacc acattgaccg cgtgtttgat | 300 |
| ggcgcccaga aactgcgtct gcagagcccg ctgaccaagg ccgaagtgga ggatattacc | 360 |
| aaacgctgcg tgagcctgag tcagctgcgc gagagcttcg tgaacatcac cattacccgc | 420 |
| ggttatggcg cccgcaaagg cgagaaagat ctgagcaaat taaccagcca gatctacatc | 480 |
| tacgccatcc cgtacctgtg ggcctttcct ccggaagagc agatcttcgg tacaagtgcc | 540 |
| attgtgccgc gtcatgttcg tcgcgcaggc cgtaataccg ttgatcctac cgttaagaac | 600 |
| taccagtggg gtgatctgac cgcagcttct tttgaagcaa aagatcgtgg cgcccgcacc | 660 |

```
gcaatcctgc tggatgcaga caactgtgtg gccgagggtc cgggctttaa cgtggtgatg    720
gtgaaggatg gcaaactgag tagcccgagc cgtaatgccc tgccgggtat tacacgtctg    780
accgtgatgg agatggccga tgaaatgggc atcgaattca ccctgcgcga tatcaccagc    840
cgtgagttat atgaggccga cgaactgatc gccgtgacca ccgaggtgg  cattaccccg    900 attaccagtc tggatggcga accgctgggc gatggtaccc ctggtcctgt gacagtggcc    960
attcgcgatc gcttttgggc catgatggat gagccgagca gtctggtgga ggccattgaa   1020
tattaa                                                               1026

<210> SEQ ID NO 60
<211> LENGTH: 1026
<212> TYPE: DNA
<213> ORGANISM: Unknown
<220> FEATURE:
<223> OTHER INFORMATION: Bacteria of the phylum Actinobacteria.

<400> SEQUENCE: 60
atgaccatta gcaaagacat tgactatagc accagcaacc tggtgagtgt ggccccgggt     60
gcaatccgtg aacctacccc ggcaggcagc gtgatccagt acagtgacta cgagctggat    120
gaaagcagcc cgtttgccgg tggtgcagcc tggattgaag gtgagtatgt tccggcagca    180
gaggcccgta ttagcctgtt tgataccggc ttcggccata gcgatgcgac ctacaccgtt    240
gcccatgttt ggcacggcaa catctttcgc ctgaaagacc acattgaccg cgtgtttgat    300
ggcgcccaga aactgcgtat acagagccag ctgaccaagg ccgaagtgga ggatattacc    360
aaacgctgcg tgagcctgag tcagctgcgc gagagcttcg tgaacatcac cattacccgc    420
ggttatggcg cccgcaaagg cgagaaaggt ctgagcaaat taaccagcca gatctacatc    480
tacgccatcc cgtacctgtg ggcctttcct ccggaagagc agatcttcgg tacaagtgcc    540
attgtgccgc gtcatgttcg tcgcgcaggc cgtaataccg ttgatcctac cgttaagaac    600
taccagtggg gtgatctgac cgcagcttct tttgaagcaa aagatcgtgg cgcccgcacc    660
gcaatcctgc tggatgcaga caactgtgtg gccgagggtc cgggctttaa cgtggtgatg    720
gtgaaggatg gcaaactgag tagcccgagc cgtaatgccc tgccgggtat tacacgtctg    780
accgtgatgg agatggccga tgaaatgggc atcgaattca ccctgcgcga tatcaccagc    840
cgtgagttat atgaggccga cgaactgatc gccgtgacca ccgcaggtgg  cattaccccg   900
attaccagtc tggatggcga accgctgggc gatggtaccc ctggtcctgt gacagtggcc    960
attcgcgatc gcttttgggc catgatggat gagccgagca gtctggtgga ggccattgaa   1020
tattaa                                                              1026
```

US 11,407,982 B2

TRANSAMINASE MUTANT AND USE THEREOF

CROSS-REFERENCE TO RELATED APPLICATION

This application is the U.S. National Stage Application of International Patent Application No. PCT/CN2017/109500, filed Nov. 6, 2017, the content of which is incorporated by reference in its entirety herein.

SEQUENCE LISTING

The instant application contains a Sequence Listing which has been submitted electronically in ASCII format and is hereby incorporated by reference in its entirety. Said ASCII copy is named PN125553KLY Sequence Listing.txt and is 130 kilobytes in size.

TECHNICAL FIELD

The disclosure relates to the field of biotechnologies, in particular to transaminase mutants and use thereof.

BACKGROUND

Chiral amines widely exist in the natural world, are structural units of many important bioactive molecules, and are important intermediates for synthesizing natural products and chiral drugs. Many chiral amines contain one or more chiral center, there are significant differences in pharmacological activity, metabolic process, metabolic rate and toxicity of the different chiral drugs, usually one enantiomer is effective, but the other enantiomer is low-effective or ineffective, and even toxic. Therefore, how to efficiently and stereoselectively construct compounds containing the chiral centers is of great significance in pharmaceutical research and development.

An Omega-transaminase (ω-TA) belongs to transferases, and, like other transaminases, catalyzes a process of exchange of amino and keto groups. In most cases, the Omega-transaminase refers to a class of enzymes, as long as a substrate or a product in a transamination reaction catalyzed by a certain enzyme does not contain an Alpha-amino acid, the enzyme may be called the Omega-transaminase. The Omega-transaminase uses a ketones compound as a raw material, and through stereoselective transamination, may efficiently produce the chiral amines. Because the Omega-transaminase has the characteristics of relatively cheap substrates and high-purity products, it has received increasing attention from researchers (*Green Chemistry*, 2017, 19(2): 333-360.)

However, the wild-type transaminase often has the defects of poor substrate tolerance, low activity, poor stability and the like, and is a long way from industrial applications.

SUMMARY

The disclosure aims to provide a transaminase mutant and an use thereof, as to solve a technical problem that a wild-type transaminase in an existing technology is not suitable for industrial production.

In order to achieve the above objective, according to one aspect of the disclosure, a transaminase mutant is provided. An amino acid sequence of the transaminase mutant is an amino acid sequence obtained while a mutation occurs in an amino acid sequence as shown in SEQ ID NO: 1, and the mutation at least includes one of the following mutation sites: the 19-th site, the 41-th site, the 43-th site, the 72-th site, the 76-th site, the 92-th site, the 107-th site, the 125-th site, the 132-th site, the 226-th site, the 292-th site, the 295-th site, the 308-th site, and the 332-th site; and the 19-th site is mutated to a serine, the 41-th site is mutated to a serine, the 43-th site is mutated to an asparagine, a glycine in the 72-th site is mutated to a leucine, a leucine in the 76-th site is mutated to an alanine, a lysine in the 92-th site is mutated to a glycine, a leucine in the 107-th site is mutated to an isoleucine, a serine in the 125-th site is mutated to an alanine, a serine in the 132-th site is mutated to an alanine, an alanine in the 226-th site is mutated to a glycine, a valine in the 292-th site is mutated to a cysteine, an alanine in the 295-th site is mutated to a glycine, the 308-th site is mutated to a serine, and the 332-th site is mutated to a serine; or the amino acid sequence of the transaminase mutant has the mutation sites in the mutated amino acid sequence, and has more than 80% of homology with the mutated amino acid sequence.

Further, the amino acid sequence of the transaminase mutant is an amino acid sequence as shown in SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 or SEQ ID NO: 30; or the amino acid sequence of the transaminase mutant is an amino acid sequence having more than 95% of the homology with the amino acid sequence as shown in SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 or SEQ ID NO: 30.

According to another aspect of the disclosure, a DNA molecule is provided. The DNA molecule encodes any one of the above transaminase mutants.

Further, a sequence of the DNA molecule is a sequence as shown in SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59 or SEQ ID NO: 60; or the sequence of the DNA molecule is a sequence having more than 95% of the homology with the sequence as shown in SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59 or SEQ ID NO: 60.

According to one aspect of the disclosure, a recombinant plasmid is provided. The recombinant plasmid contains any one of the above DNA molecules.

Further, the recombinant plasmid is pET-22b(+), pET-22b (+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a (+), pET-25b(+), pET-26b(+), pET-27b(+), pET-28a(+), pET-29a(+), pET-30a(+), pET-31b(+), pET-32a(+), pET-35b (+), pET-38b(+), pET-39b(+), pET-40b(+), pET-41a(+), pET-41b(+), pET-42a(+), pET-43a(+), pET-43b(+), pET-44a (+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

According to one aspect of the disclosure, a host cell is provided. The host cell contains any one of the above recombinant plasmids.

Further, the host cell includes a prokaryotic cell, yeast or a eukaryocyte cell; preferably the prokaryotic cell is an *Escherichia coli* BL21 cell or an *Escherichia coli* DH5α competent cell.

According to one aspect of the disclosure, a method for providing a chiral amine is provided. The method includes a step of performing a catalytic transamination reaction on a ketones compound and an amino donor by a transaminase, herein the transaminase is any one of the above transaminase mutants.

The ketones compound is

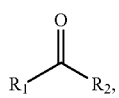

herein, each of $R_1$ and $R_2$ is independently $C_1$-$C_8$ alkyl, $C_5$-$C_{10}$ cycloalkyl, $C_5$-$C_{10}$ aryl or $C_5$-$C_{10}$ heteroaryl, or the $R_1$ and the $R_2$ and the carbon on the carbonyl group together form $C_5$-$C_{10}$ heterocyclyl, $C_5$-$C_{10}$ carbocyclyl or the $C_5$-$C_{10}$ heteroaryl, each of heteroatoms in the $C_5$-$C_{10}$ heterocyclyl and the $C_5$-$C_{10}$ heteroaryl is independently selected from at least one of nitrogen, oxygen and sulfur, and each of an aryl in the $C_5$-$C_{10}$ aryl, heteroaryl in the $C_5$-$C_{10}$ heteroaryl, carbocyclyl in the $C_5$-$C_{10}$ carbocyclyl or heterocyclyl in the $C_5$-$C_{10}$ heterocyclyl is independently unsubstituted or substituted by at least one group of halogen, alkoxy or alkyl, preferably, the ketones compound is

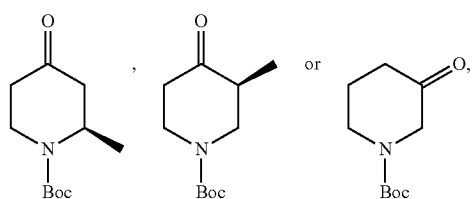

a product of the transaminase reaction is

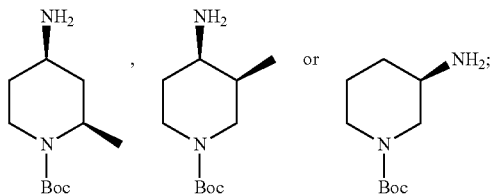

more preferably, the ketones compound is

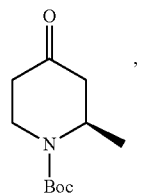

and the product of the transaminase reaction is

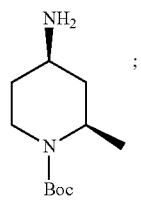

preferably, the amino donor is an isopropylamine.

The above transaminase mutant of the disclosure is obtained by mutating the transaminase as shown in SEQ ID NO: 1 through a method of site-directed mutation and through a method of directed screening, thereby changing the amino acid sequence thereof, realizing a change of protein structure and function, and acquiring the transaminase with the above mutation sites. the transaminase mutant of the disclosure has an advantage of greatly improving enzymatic activity, the enzymatic activity thereof is improved by multiple times relative to a transaminase parent, and enzyme specificity is also improved correspondingly, thereby the cost in chiral amine industrial production is greatly reduced.

DETAILED DESCRIPTION OF THE EMBODIMENTS

It is to be noted that embodiments in the present application and features in the embodiments may be mutually combined in the case without conflicting. The disclosure is described in detail below in combination with the embodiments.

An aminotransferase derived from actinomycetes *Actinobacteria* sp. (also called a transaminase) high-selectively catalyzes transform

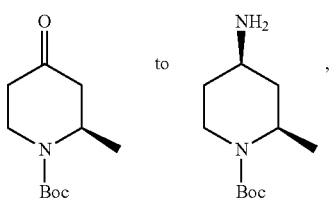

but it is lower in activity, poorer in stability, and more in added enzyme amount during a reaction. The inventor of the disclosure, through a method of directed evolution, improves activity and stability of the aminotransferase derived from the *Actinobacteria* sp., and reduces a usage amount of the enzyme. Firstly, a mutation site is introduced in the aminotransferase derived from the *Actinobacteria* sp. through a mode of a whole-plasmid PCR, activity and stability of a mutant are detected, and the mutant with the improved activity and stability is selected.

An aminotransferase derived from *Actinobacteria* sp. is used as a template, 53 pairs of site-directed mutation primers (P19S, F71Y, G72Y, G72L, H73T, L76A, L76V, V80T, K92G, K92D, L105I, L105M, L107I, F133M, N135T, N135S, T137S, G147F, Y161S, I163C, I163V, A180L, S210I, S210V, T220L, T220A, A226C, A226G, N228G, P234S, S280L, Y284L, T293S, A295G, P308S, V317I, P332S, V31Y, E41S, S43N, G101S, K121V, R122D, C123M, S125A, S132A, S156N, H185T, A208R, K245V, L260K, F273V and V292C) are designed, a measure of site-directed mutation is used, and pET-22b(+) is used as an expression vector, as to obtain a mutation plasmid with a target gene.

Herein, the site-directed mutation is that: through methods of a polymerase chain reaction (PCR) and the like, a required change (generally a change of representing a beneficial direction) is introduced in a target DNA fragment (may be a genome, or may be a plasmid), including addition, deletion, point mutation and the like of a basic group. The site-directed mutation is capable of rapidly and efficiently improving characters and representation of a target protein expressed by a DNA, and is a very useful tool in gene research work.

The method for introducing the site-directed mutation by using the whole-plasmid PCR is simple and effective, and is a method used more at present. A principle thereof is that after a pair of primers (forward and reverse) containing mutation sites are annealed with a template plasmid, "cyclic extension" is performed by using a polymerase, and the so-called cyclic extension is that the polymerase extends the primer according to the template, is returned to a 5'-terminal of the primer and terminated after one circle, and subjected to a cycle of repeatedly heated and annealed extension, this reaction is different from rolling circle amplification, and does not form multiple tandem copies. Extension products of the forward and reverse primers are paired to form an open-circle plasmid with an incision after annealed. A Dpn I enzyme-digested extension product, because the original template plasmid is derived from conventional *Escherichia coli*, is modified by dam methylation, and is sensitive to Dpn I so as to be shredded, but a plasmid with a mutant sequence synthesized in vitro is not cut because it is not methylated, so it may be successfully transformed in subsequent transformation, and a clone of a mutant plasmid may be obtained.

The above mutant plasmid is transformed into an *Escherichia coli* cell, and over-expressed in the *Escherichia coli*. After that, a crude enzyme is obtained through a method of ultrasonic cell-break. An optimum condition of transaminase induced expression is as follows: 25 DEG C, and inducing overnight in 0.1 mM of IPTG.

Computer simulation analysis is performed on a three-dimensional structure of the transaminase by using software, G72L is positioned near an active pocket, and near a protein dimer interface, binding capacity of a protein dimer is reinforced, so a protein is more stable. V292C is positioned in a binding domain of a cofactor PLP, and binding capacity of the PLP may also be reinforced. A226G and A295G are positioned near a substrate binding pocket, an orientation of a substrate is affected possibly, and catalytic efficiency is reinforced.

According to a typical implementation of the disclosure, a transaminase mutant is provided. An amino acid sequence of the transaminase mutant is an amino acid sequence obtained which a mutation occurs in an amino acid sequence as shown in SEQ ID NO: 1, and the mutation at least includes one of the following mutation sites: the 19-th site, the 41-th site, the 43-th site, the 72-th site, the 76-th site, the 92-th site, the 107-th site, the 125-th site, the 132-th site, the 226-th site, the 292-th site, the 295-th site, the 308-th site, and the 332-th site; and the 19-th site is mutated into a serine, the 41-th site is mutated into a serine, the 43-th site is mutated into an asparagine, a glycine in the 72-th site is mutated into a leucine, a leucine in the 76-th site is mutated into an alanine, a lysine in the 92-th site is mutated into a glycine, a leucine in the 107-th site is mutated into an isoleucine, a serine in the 125-th site is mutated into an alanine, a serine in the 132-th site is mutated into an alanine, an alanine in the 226-th site is mutated into a glycine, a valine in the 292-th site is mutated into a cysteine, an alanine in the 295-th site is mutated into a glycine, the 308-th site is mutated into a serine, and the 332-th site is mutated into a serine; or the amino acid sequence of the transaminase mutant has the mutation sites in the mutated amino acid sequence, and has more than 80% of homology with the mutated amino acid sequence.

The term "homology" used in the disclosure has a meaning generally known in the art, and those skilled in the art are also familiar with rules and standards for measuring the homology between different sequences. The sequences defined by the disclosure with different degrees of the homology must also have improved transaminase activity at the same time. Those skilled in the art, under the guidance of the content disclosed by the present application, may obtain the amino acid sequence of the transaminase mutant which is the amino acid sequence having the mutation sites in the above mutated amino acid sequence, and having more than 80% of the homology with the mutated amino acid sequence.

Preferably, the amino acid sequence of the transaminase mutant is an amino acid sequence as shown in SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 or SEQ ID NO: 30; or the amino acid sequence of the transaminase mutant is an amino acid sequence having more than 95% of the homology with the amino acid sequence as shown in SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO:

13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 or SEQ ID NO: 30.

The term "homology" used in the disclosure has a meaning generally known in the art, and those skilled in the art are also familiar with rules and standards for measuring the homology between different sequences. The sequences defined by the disclosure with different degrees of the homology must also have improved transaminase activity at the same time. In the above implementation, preferably the amino acid sequence of the transaminase mutant has more than 95% of the homology with the amino acid sequence as shown in SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 or SEQ ID NO: 30, and has or encodes the amino acid sequence with the improved transaminase activity. Those skilled in the art, under the guidance of the content disclosed by the present application, may obtain such a mutant sequence.

The above transaminase mutant of the disclosure is obtained by mutating the transaminase as shown in SEQ ID NO: 1 (a coding DNA is SEQ ID NO: 31) through a method of site-directed mutation and through a method of directed screening, thereby changing the amino acid sequence thereof, realizing a change of protein structure and function, and acquiring the transaminase with the above mutation sites. the transaminase mutant of the disclosure has an advantage of greatly improving enzymatic activity, the enzymatic activity thereof is improved by 6 times relative to a transaminase parent, and enzyme specificity is also improved correspondingly, thereby the cost in chiral amine industrial production is greatly reduced.

According to a typical implementation of the disclosure, the 72-th site of the transaminase derived from the *Actinobacteria* sp. is mutated from a glycine to a leucine; or the 76-th site is mutated from a leucine to an alanine; or the 107-th site is mutated from a leucine to an isoleucine; or the 125-th site is mutated from a serine to an alanine; or the 132-th site is mutated from a serine to an alanine; or the 76-th site is mutated from the leucine to the alanine, the 125-th site is mutated from the serine to the alanine and the 226-th site is mutated from an alanine to a glycine; or the 76-th site is mutated from the leucine to the alanine, the 107-th site is mutated from a leucine to an isoleucine, the 125-th site is mutated from the serine to the alanine and the 226-th site is mutated from the alanine to the glycine; or the 76-th site is mutated from the leucine to the alanine, the 125-th site is mutated from the serine to the alanine, the 132-th site is mutated from the serine to the alanine and the 226-th site is mutated from the alanine to the glycine; or the 76-th site is mutated from the leucine to the alanine, the 107-th site is mutated from the leucine to the isoleucine, the 125-th site is mutated from the serine to the alanine, the 132-th site is mutated from the serine to the alanine and the 226-th site is mutated from the alanine to the glycine.

According to a typical implementation of the disclosure, a DNA molecule is provided. The DNA molecule codes the above transaminase mutant. Preferably, a sequence of the DNA molecule is a sequence as shown in SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59 or SEQ ID NO: 60; or the sequence of the DNA molecule is a sequence having more than 95% of the homology with the sequence as shown in SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59 or SEQ ID NO: 60. The transaminase coded by the above DNA is capable of improving enzymatic activity and stability of the enzyme, reducing an added enzyme amount in industrial production of chiral amines, and reducing post-treatment difficulty.

The above DNA molecule of the disclosure may also exist in the form of an "expression cassette". The "expression cassette" refers to a linear or circular nucleic acid molecule that encompasses DNA and RNA sequences capable of guiding expression of a specific nucleotide sequence in an appropriate host cell. Generally, including a promoter which is effectively linked with a target nucleotide, it is optionally effectively linked with a termination signal and/or other control elements. The expression cassette may also include a sequence required for proper translation of the nucleotide sequence. A coding region usually encodes a target protein, but also encodes a target function RNA in a sense or antisense direction, for example an antisense RNA or an untranslated RNA. The expression cassette including a target polynucleotide sequence may be chimeric, which means that at least one of components thereof is heterologous to at least one of the other components thereof. The expression cassette may also be existent naturally, but obtained with effective recombinant formation for heterologous expression.

According to a typical implementation of the disclosure, a recombinant plasmid is provided. The recombinant plasmid contains any one of the above DNA molecules. The DNA molecule in the above recombinant plasmid is placed in a proper position of the recombinant plasmid, so that the above DNA molecule may be correctly and smoothly copied, transcribed or expressed.

Although a qualifier used in the disclosure while the above DNA molecule is defined is "contain", it does not mean that other sequences which are not related to a function thereof may be arbitrarily added to both ends of the DNA sequence. Those skilled in the art know that in order to meet the requirements of recombination operations, it is necessary to add suitable enzyme digestion sites of a restriction enzyme at two ends of the DNA sequence, or additionally increase a start codon, a termination codon and the like, therefore, if the closed expression is used for defining, these situations may not be covered truly.

The term "plasmid" used in the disclosure includes any plasmids, cosmids, bacteriophages or *agrobacterium* binary nucleic acid molecules in double-strand or single-strand linear or circular form, preferably a recombinant expression plasmid, which may be a prokaryotic expression plasmid or may be a eukaryotic expression plasmid, preferably the prokaryotic expression plasmid, in some implementation, the recombinant expression plasmid is selected from pET-22b(+), pET-22b(+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19. More preferably, the above recombinant expression plasmid is pET-22b(+).

According to a typical implementation of the disclosure, a host cell is provided, and the host cell contains any one of the above recombinant plasmids. The host cell suitable for the disclosure includes, but not limited to, a prokaryotic cell, yeast or a eukaryotic cell. Preferably the prokaryotic cell is a eubacterium, for example a Gram-negative bacterium or a Gram-positive bacterium. More preferably the prokaryotic cell is an *Escherichia coli* BL21 cell or an *Escherichia coli* DH5α competent cell.

According to a typical implementation of the disclosure, a method for producing a chiral amine is provided. The method includes a step of performing a catalytic transamination reaction on a ketones compound and an amino donor by a transaminase, herein the transaminase is any one of the above transaminase mutants. Because the above transaminase mutant of the disclosure has the higher enzyme catalytic activity, the chiral amine prepared by using the transaminase mutant of the disclosure is capable of reducing the production cost, and an ee value of the obtained chiral amine is greater than 99%, and a de value is 98%.

According to a typical implementation of the disclosure, the ketones compound is

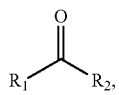

herein, each of $R_1$ and $R_2$ is independently $C_1$-$C_8$ alkyl, $C_5$-$C_{10}$ cycloalkyl, $C_5$-$C_{10}$ aryl or $C_5$-$C_{10}$ heteroaryl, or the $R_1$ and the $R_2$ and the carbon on the carbonyl group together form a $C_5$-$C_{10}$ heterocyclyl, a $C_5$-$C_{10}$ carbocyclyl or the $C_5$-$C_{10}$ heteroaryl, each of heteroatoms in the $C_5$-$C_{10}$ heterocyclyl and the $C_5$-$C_{10}$ heteroaryl is independently selected from at least one of nitrogen, oxygen and sulfur, and each of an aryl in the $C_5$-$C_{10}$ aryl, heteroaryl in the $C_5$-$C_{10}$ heteroaryl, carbocyclyl in the $C_5$-$C_{10}$ carbocyclyl or heterocyclyl in the $C_5$-$C_{10}$ heterocyclyl is independently unsubstituted or substituted by at least one group of halogen, alkoxy or alkyl, preferably, the ketones compound is

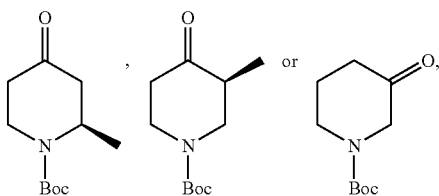

a product of the transaminase reaction is

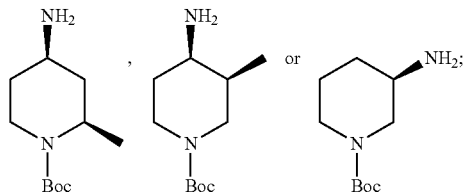

more preferably, the ketones compound is

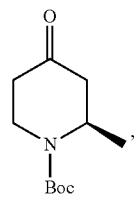

and the product of the transaminase reaction is

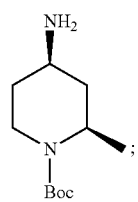

preferably, the amino donor is an isopropylamine.

Beneficial effects of the disclosure are further described below in combination with the embodiments.

It is well-known to those skilled in the art that many modifications may be made to the disclosure without departing from spirit of the disclosure, and such modifications also fall within a scope of the disclosure. In addition, the following experimental modes are conventional methods unless otherwise specified, and the experimental materials used may be easily obtained from commercial companies unless otherwise specified.

Main raw materials mentioned in the following embodiments are as follows:

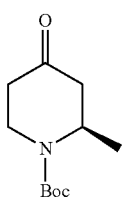

Main raw material 1: tert-butyl(2S)-2-methyl-4-oxopiperidine-1-carboxylate, CAS 790667-43-5.

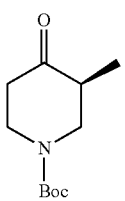

Main raw material 2: (S)-tert-butyl 3-methyl-4-oxopiperidine-1-carboxylate.

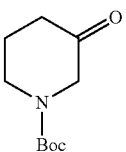

Main raw material 3: N-Boc-3-piperidone, CAS 98977-36-7.

Embodiment 1

In 10 mL of a reaction flask, 40 mg of an isopropylamine is added to 1 mL of 0.2 M phosphate buffer solution, a pH is adjusted to be 7.0-7.5, 120 mg of a transaminase having an amino acid sequences as shown in SEQ ID NO: 1 is added, and 0.4 mg of a pyridoxal phosphate is added, after uniformly mixed, 40 mg of

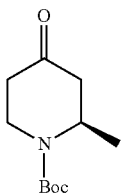

dissolved in 0.2 mL of DMSO is dropwise added, a pH of a system is 7.0-7.5, and stirring is performed for 16 h at 35+(−)3 DEG C. of a constant temperature. A transformation rate of the system is detected by GC. According to the above steps, the mutant transaminases of which sequence numbers are SEQ ID NO: 13-26 are successively reacted, and data is as shown in Table 1 below:

TABLE 1

| Sequence number | Mutation site | 16 h | Enzyme dosage |
|---|---|---|---|
| SEQ ID NO: 1 | N/A | 21.3% | 3 wt |
| SEQ ID NO: 13 | G72L | 36.8% | 2 wt |
| SEQ ID NO: 14 | L76A | 47.1% | 2 wt |
| SEQ ID NO: 15 | L107I | 47.7% | 2 wt |
| SEQ ID NO: 16 | S125A | 38.9% | 2 wt |
| SEQ ID NO: 17 | S132A | 52.8% | 2 wt |
| SEQ ID NO: 18 | K92G | 39.5% | 2 wt |
| SEQ ID NO: 19 | A226G | 37.6% | 2 wt |
| SEQ ID NO: 20 | V292C | 42.1% | 2 wt |
| SEQ ID NO: 21 | A295G | 44.2% | 2 wt |
| SEQ ID NO: 22 | P19S | 40.1% | 2 wt |
| SEQ ID NO: 23 | E41S | 41.6% | 2 wt |

TABLE 1-continued

| Sequence number | Mutation site | 16 h | Enzyme dosage |
|---|---|---|---|
| SEQ ID NO: 24 | S43N | 39.6% | 2 wt |
| SEQ ID NO: 25 | P308S | 42.4% | 2 wt |
| SEQ ID NO: 26 | P332S | 45.7% | 2 wt |

Herein, 16 h refers to the reaction for 16 h, the percentage refers to the transformation rate, and 2 wt is that a weight of an enzyme added is 2 times greater than a weight of a substrate.

The transformation effect of a single-point mutant is improved relative to a parent, but does not reach an ideal effect.

Embodiment 2

Generally, it is difficult to have a large difference in mutant property of a single-point mutation compared with a parent, a combination of mutation points may obtain a better mutant. Therefore, mutation sites are randomly recombined through a DNA shuffling method, a mutation library is established, and then screening is performed to try to get the better mutant.

DNA shuffling is a sexual recombination of genes performed in molecular level. A group of homologous genes are digested into random fragments by using a nuclease I, a library is formed by these random fragments, and these random fragments are used as primers and templates mutually for performing PCR amplification. While one gene copy fragment is served as a primer of another gene copy, template interchange and gene recombination occur.

An enzyme solution preparation method is as follows: remove a supernatant culture medium in a 96-pore plate by centrifugation, add 200 μl of enzymolysis solution (2 mg/mL of a lysozyme, 0.5 mg/mL of a polymyxin, and pH=7.0) to per pore, incubate at 37 DEG C. for 3 h.

A high-throughput screening method is as follows: 250 μl of an activity measuring system: 0.27 mg/mL of final concentration of

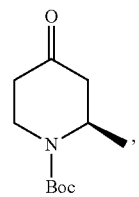

12.24 mg/mL of final concentration of 4-nitrophenethylamine hydrochloride, 0.01 mg/mL of final concentration of PLP, 45 μl of an addition amount of enzyme solution, pH=8.0, and 30 DEG C. of a temperature.

Shake-flask culture is performed on a mutant obtained by screening, and then an amplification reaction is performed.

An optimum condition of transaminase induced expression is as follows: 25 DEG C., and inducing overnight in 0.1 mM of IPTG.

SEQ ID NO: 1 and prepared multi-site mutants SEQ ID NO: 2-12 and 27-30 are reacted as below:

In 10 mL of a reaction flask, 40 mg of an isopropylamine is added to 1 mL of 0.2 M phosphate buffer solution, a pH is adjusted to be 7.0-7.5, 40 mg of a transaminase by mass is added, and 0.4 mg of a pyridoxal phosphate is added, after uniformly mixed, 40 mg of a main raw material 1 dissolved in 0.2 mL of DMSO is dropwise added, a pH of a system is 7.0-7.5, and stirring is performed for 16-64 h at 35+(-)3 DEG C of a constant temperature. A transformation rate of the system is detected by GC. The mutants are reacted, and data is as shown in Table 2 below:

TABLE 2

| Sequence number | Mutation site | 16 h | 64 h | Enzyme dosage |
|---|---|---|---|---|
| SEQ ID NO: 1 | N/A | 21.3% | 35.7% | 3 wt |
| SEQ ID NO: 2 | L76A + R130A + V292C + A295G | 38.5% | 84.1% | 1 wt |
| SEQ ID NO: 3 | L107I + A295G | 42.1% | 87.2% | 1 wt |
| SEQ ID NO: 4 | S43N + G72L + A295G | 52.1% | 87.3% | 1 wt |
| SEQ ID NO: 5 | D96N + L104I + A295G | 47.4% | 84.2% | 1 wt |
| SEQ ID NO: 6 | L76A + S125A + A226G + A295G | 63.6% | 92.5% | 1 wt |
| SEQ ID NO: 7 | L76A + S125A + A226G + S132A + A295G | 65.8% | 96.8% | 1 wt |
| SEQ ID NO: 8 | S132A + A295G | 60.5% | 89.3% | 1 wt |
| SEQ ID NO: 9 | G72L + A295G | 45.2% | 88.1% | 1 wt |
| SEQ ID NO: 10 | G72L + A295G + S132A | 47.8% | 91.3% | 1 wt |
| SEQ ID NO: 11 | G72L + V292C + A295G | 55.4% | 86.5% | 1 wt |
| SEQ ID NO: 12 | G72L + L76A + V292C + A295G | 64.7% | 94.3% | 1 wt |
| SEQ ID NO: 27 | L76A + L107I + P110Q | 37.2% | 65.3% | 1 wt |
| SEQ ID NO: 28 | L76A + S125A + A226G | 41.8% | 78.6% | 1 wt |
| SEQ ID NO: 29 | L76A + T79S + A295G | 47.5% | 85.6% | 1 wt |
| SEQ ID NO: 30 | L76A + L107I + P110Q + D150G | 36.3% | 69.7% | 1 wt |

Embodiment 3

Two parts of transaminases in SEQ ID NO: 1 are taken, and a mass of each of the two parts of the transaminases is 40 mg, herein one part is incubated for 2 h at 4 DEG C., and the other part is incubated for 2 h at 50 DEG C., and then a reaction is performed according to the following system.

In 10 mL of a reaction flask, 40 mg of an isopropylamine is added to 1 mL of 0.2 M phosphate buffer solution, a pH is adjusted to be 7.0-7.5, 40 mg of a transaminase having an amino acid sequences as shown in SEQ ID NO: 7 by mass is added, and 0.4 mg of a pyridoxal phosphate is added, after uniformly mixed, 40 mg of a main raw material 1 dissolved in 0.2 mL of DMSO is dropwise added, a pH of a system is 7.0-7.5, and stirring is performed for 16 h at 35+(-)3 DEG C. of a constant temperature.

A transformation rate of the system is detected by GC, mutant stability is expressed as a percentage of a transaminase transformation rate of incubated at 50 DEG C. accounting for a transaminase transformation rate of incubated at 4 DEG C.

Stability data of SEQ ID NO: 1-30 is as shown in Table 3 below:

TABLE 3

| Sequence number | Mutation site | Residual activity (%) |
|---|---|---|
| SEQ ID NO: 1 | N/A | 51.2 |
| SEQ ID NO: 2 | L76A + R130A + V292C + A295G | 42.5 |
| SEQ ID NO: 3 | L107I + A295G | 76.8 |
| SEQ ID NO. 4 | S43N + G72L + A295G | 85.1 |
| SEQ ID NO: 5 | D96N + L104I + A295G | 48.5 |
| SEQ ID NO: 6 | L76A + S125A + A226G + A295G | 58.6 |
| SEQ ID NO: 7 | L76A + S125A + A226G + S132A + A295G | 61.3 |
| SEQ ID NO: 8 | S132A + A295G | 50.5 |
| SEQ ID NO: 9 | G72L + A295G | 81.2 |
| SEQ ID NO: 10 | G72L + A295G + S132A | 91.5 |
| SEQ ID NO: 11 | G72L + V292C + A295G | 75.2 |
| SEQ ID NO: 12 | G72L + L76A + V292C + A295G | 73.4 |
| SEQ ID NO: 13 | G72L | 66.8 |
| SEQ ID NO: 14 | L76A | 68.9 |
| SEQ ID NO: 15 | L107I | 59.3 |
| SEQ ID NO: 16 | S125A | 36.8 |
| SEQ ID NO: 17 | S132A | 47.3 |
| SEQ ID NO: 18 | K92G | 39.5 |
| SEQ ID NO: 19 | A226G | 35.6 |
| SEQ ID NO: 20 | V292C | 45.8 |
| SEQ ID NO: 21 | A295G | 61.2 |
| SEQ ID NO: 22 | P19S | 62.3 |
| SEQ ID NO: 23 | E41S | 65.7 |
| SEQ ID NO: 24 | S43N | 55.3 |
| SEQ ID NO: 25 | P308S | 68.2 |
| SEQ ID NO: 26 | P332S | 57.7 |
| SEQ ID NO: 27 | L76A + L107I + P110Q | 78.5 |
| SEQ ID NO: 28 | L76A + S125A + A226G | 40.3 |
| SEQ ID NO: 29 | L76A + T79S + A295G | 43.6 |
| SEQ ID NO: 30 | L76A + L107I + P110Q + D150G | 69.4 |

Embodiment 4

In 1000 mL of a reaction flask, 4 g of an isopropylamine is added to 100 mL of 0.2 M phosphate buffer solution, a pH is adjusted to be 7.0-7.5, 0.4 g freeze-dried powder of transaminase having an amino acid sequences as shown in SEQ ID NO: 7 by mass is added, and 40 mg of a pyridoxal phosphate is added, after uniformly mixed, 4 g of a main raw material 1 dissolved in 20 mL of DMSO is dropwise added, a pH of a system is 7.0-7.5, and stirring is performed for 64 h at 35+(-)3 DEG C. of a constant temperature. A transformation rate detected by a HPLC is 98.2%, after a reaction is finished, 100 mL of ethyl acetate is added for extracting for 3 times, after extraction organic phases are merged, a magnesium sulfate is added for drying, rotary evaporation is performed until it is dried, and 3.62 g of a product is obtained, herein a yield is 90.2%, and a e.e. value is 99%.

According to the above steps, the mutant transaminases of which sequence numbers are SEQ ID NO: 6, 7, 10 and 12 are successively reacted, and data is as shown in Table 4 below:

TABLE 4

| Sequence number | Mutation site | Yield | e.e. |
|---|---|---|---|
| SEQ ID NO: 6 | L76A + S125A + A226G + A295G | 89.5% | 99% |
| SEQ ID NO: 7 | L76A + S125A + A226G + S132A + A295G | 90.2% | 99% |
| SEQ ID NO: 10 | G72L + A295G + S132A | 88.9% | 99% |
| SEQ ID NO: 12 | G72L + L76A + V292C + A295G | 89.3% | 99% |

Embodiment 5

In 1000 mL of a reaction flask, 4 g of an isopropylamine is added to 100 mL of 0.2 M phosphate buffer solution, a pH is adjusted to be 7.0-7.5, 0.4 g freeze-dried powder of transaminase having an amino acid sequences as shown in SEQ ID NO: 7 by mass is added, and 40 mg of a pyridoxal phosphate is added, after uniformly mixed, 4 g of a main raw material 2 dissolved in 20 mL of DMSO is dropwise added, a pH of a system is 7.0-7.5, and stirring is performed for 64 h at 35+(−)3 DEG C. of a constant temperature. A transformation rate detected by a HPLC is 99.1%, after a reaction is finished, 100 mL of ethyl acetate is added for extracting for 3 times, after extraction organic phases are merged, a magnesium sulfate is added for drying, rotary evaporation is performed until it is dried, and 3.75 g of a product is obtained, herein a yield is 93.8%, and a e.e. value is 99%.

Embodiment 6

In 1000 mL of a reaction flask, 4 g of an isopropylamine is added to 100 mL of 0.2 M phosphate buffer solution, a pH is adjusted to be 7.0-7.5, 0.2 g freeze-dried powder of transaminase having an amino acid sequences as shown in SEQ ID NO: 7 by mass is added, and 40 mg of a pyridoxal phosphate is added, after uniformly mixed, 4 g of a main raw material 3 dissolved in 20 mL of DMSO is dropwise added, a pH of a system is 7.0-7.5, and stirring is performed for 64 h at 35+(−)3 DEG C. of a constant temperature. A transformation rate detected by a HPLC is 99.5%, after a reaction is finished, 100 mL of ethyl acetate is added for extracting for 3 times, after extraction organic phases are merged, a magnesium sulfate is added for drying, rotary evaporation is performed until it is dried, and 3.79 g of a product is obtained, herein a yield is 94.8%, and a e.e. value is 99%.

It may be observed from the above description that the above embodiments of the disclosure achieve the following technical effects: the above transaminase mutant of the disclosure is obtained by mutating the transaminase as shown in SEQ ID NO: 1 through a method of site-directed mutation and through a method of directed screening, thereby changing the amino acid sequence thereof, realizing a change of protein structure and function, and acquiring the transaminase with the above mutation sites. the transaminase mutant of the disclosure has an advantage of greatly improving enzymatic activity, and enzyme specificity is also improved correspondingly, thereby the cost in chiral amine industrial production is greatly reduced.

The above are merely the preferable embodiments of the disclosure, and are not intended to limit the disclosure. Various modifications and changes may be made to the disclosure by those skilled in the art. Any modifications, equivalent replacements, improvements and the like made within spirit and principles of the disclosure shall be included in a scope of protection of the disclosure.

What is claimed is:

1. A transaminase mutant, wherein an amino acid sequence of the transaminase mutant is the amino acid sequence as shown in SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 21 or SEQ ID NO: 29.

2. A method for producing chiral amines, comprising a step of performing a transamination of one or more ketone compounds and one or more amino donors catalysed by the transaminase mutant of claim 1.

3. The method of claim 2, wherein the ketone compound is

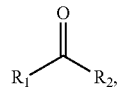

wherein $R_1$ and $R_2$, independently from each other, are $C_1$-$C_8$ alkyl, $C_5$-$C_{10}$ cycloalkyl, $C_5$-$C_{10}$ aryl or $C_5$-$C_{10}$ heteroaryl, or $R_1$ and $R_2$ and the carbon on the carbonyl group together form $C_5$-$C_{10}$ heterocyclyl, $C_5$-$C_{10}$ carbocyclic or $C_5$-$C_{10}$ heteroaryl, each heteroatom of the $C_5$-$C_{10}$ heterocyclyl and $C_5$-$C_{10}$ heteroaryl is independently selected from at least one of nitrogen, oxygen and sulphur, the aryl group of $C_5$-$C_{10}$ aryl, the heteroaryl group of $C_5$-$C_{10}$ heteroaryl, the carbocyclic group of $C_5$-$C_{10}$ carbocyclic or the heterocyclyl group of $C_5$-$C_{10}$ cycloalkyl is each independently unsubstituted or is substituted by at least one group of halogen, alkoxy or alkyl.

4. The method of claim 3, wherein, the ketone compound is

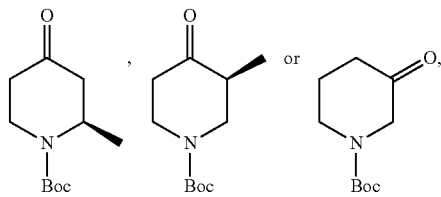

and a transamination product is

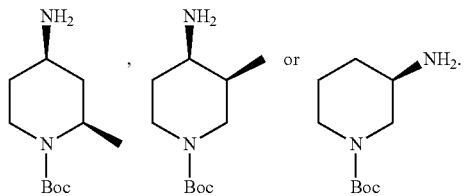

5. The method of claim 4, wherein the ketone compound is

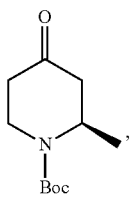

and the transamination product is

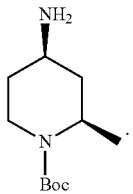

6. The method of claim 3, wherein the amino donor is isopropylamine.

* * * * *